US007657479B2

(12) United States Patent
Henley

(10) Patent No.: US 7,657,479 B2
(45) Date of Patent: Feb. 2, 2010

(54) METHOD AND SYSTEM FOR PROVISION AND ACQUISITION OF MEDICAL SERVICES AND PRODUCTS

(75) Inventor: Julian L. Henley, Guilford, CT (US)

(73) Assignee: PriceDoc, Inc., Solana Beach, CA (US)

( * ) Notice: Subject to any disclaimer, the term of this patent is extended or adjusted under 35 U.S.C. 154(b) by 2136 days.

(21) Appl. No.: 09/725,142

(22) Filed: Nov. 29, 2000

(65) Prior Publication Data

US 2002/0065758 A1  May 30, 2002

Related U.S. Application Data

(60) Provisional application No. 60/186,542, filed on Mar. 2, 2000, provisional application No. 60/201,021, filed on May 1, 2000, provisional application No. 60/222,648, filed on Aug. 3, 2000.

(51) Int. Cl.
*G06Q 40/00* (2006.01)
(52) U.S. Cl. ............... 705/37; 705/1; 705/2; 705/3; 705/4; 705/35
(58) Field of Classification Search .......... 705/37, 705/35, 1–4
See application file for complete search history.

(56) References Cited

U.S. PATENT DOCUMENTS

| 5,918,208 | A | | 6/1999 | Javitt | |
|---|---|---|---|---|---|
| 5,964,700 | A | | 10/1999 | Tallman et al. | |
| 5,995,939 | A | | 11/1999 | Berman et al. | |
| 6,006,191 | A | * | 12/1999 | DiRienzo | 705/2 |
| 6,014,629 | A | | 1/2000 | DeBruin-Ashton | |
| 6,035,276 | A | * | 3/2000 | Newman et al. | 705/2 |
| 6,035,288 | A | | 3/2000 | Solomon | |
| 6,366,891 | B1 | * | 4/2002 | Feinberg | 705/37 |
| 6,415,270 | B1 | * | 7/2002 | Rackson et al. | 705/36 R |
| 6,757,898 | B1 | * | 6/2004 | Ilsen et al. | 709/203 |
| 7,467,113 | B2 | * | 12/2008 | McFarlin et al. | 705/59 |
| 7,529,682 | B2 | * | 5/2009 | Geller et al. | 705/1 |
| 7,593,952 | B2 | * | 9/2009 | Soll et al. | 707/102 |

OTHER PUBLICATIONS

Santoli, L., Bid For Surgery, Web Site Auction to Empower Healthcare Consumers, Nov. 15, 1999, Medicine Online Puclic Relations.*
Business Editors & High Tech Writers, MedLawPlus.com Launches the Web's First Bidding System for Medical, Legal, and Accounting Services Utilizing a Request for Proposal Process in NYC, Business Wire, New York: Feb. 9, 2000. p. 1.*

* cited by examiner

*Primary Examiner*—Stefanos Karmis
(74) *Attorney, Agent, or Firm*—Nixon & Vanderhye P.C.

(57) ABSTRACT

Transactional costs associated with providing professional services are reduced by allowing prospective patients/clients (bidders) and professional service providers to negotiate competitively for desired fees for proffered services through an interactive on-line communications network such as the Internet. A transaction system server handles online communications and procedures for conducting auctions for delivery of proffered services and maintains a registration database of service providers and bidders. An authentication/qualifier engine automatically researches and verifies service provider credentials and background information upon registration of a service provider with the system. A service feedback interface and database are provided for handling online feedback information and comments from patients/clients and providers regarding the complexity and quality of services received or provided.

33 Claims, 21 Drawing Sheets

EXAMPLE TRANSACTION SYSTEM OVERVIEW DIAGRAM

FIG. 3  FACILITY REVENUE FORECAST

| MONTH | | $/HC | $/HR | $/HR-$/HC |
|---|---|---|---|---|
| | J | 280 | 250 | -30 |
| | F | 280 | 280 | 0 |
| | M | 280 | 240 | -40 |
| | A | 280 | 210 | -70 |
| | M | 280 | 240 | -40 |
| | J | 280 | 280 | 0 |
| | J | 280 | 300 | 20 |
| | A | 280 | 240 | -40 |
| | S | 280 | 200 | -80 |
| | O | 280 | 240 | -40 |
| | N | 280 | 295 | 15 |
| | D | 280 | 295 | 15 |

FIG. 4  PRICING DATABASE

| PROCEDURE | STANDARD FEE | TIME (H) |
|---|---|---|
| LIPOSUCTION | $5000 | 1.75 |
| RHINOPLASTY | 5000 | 1.75 |
| BREASTS AUGMENT | 8000 | 3.0 |

EXAMPLE TRANSACTION SYSTEM OVERVIEW DIAGRAM

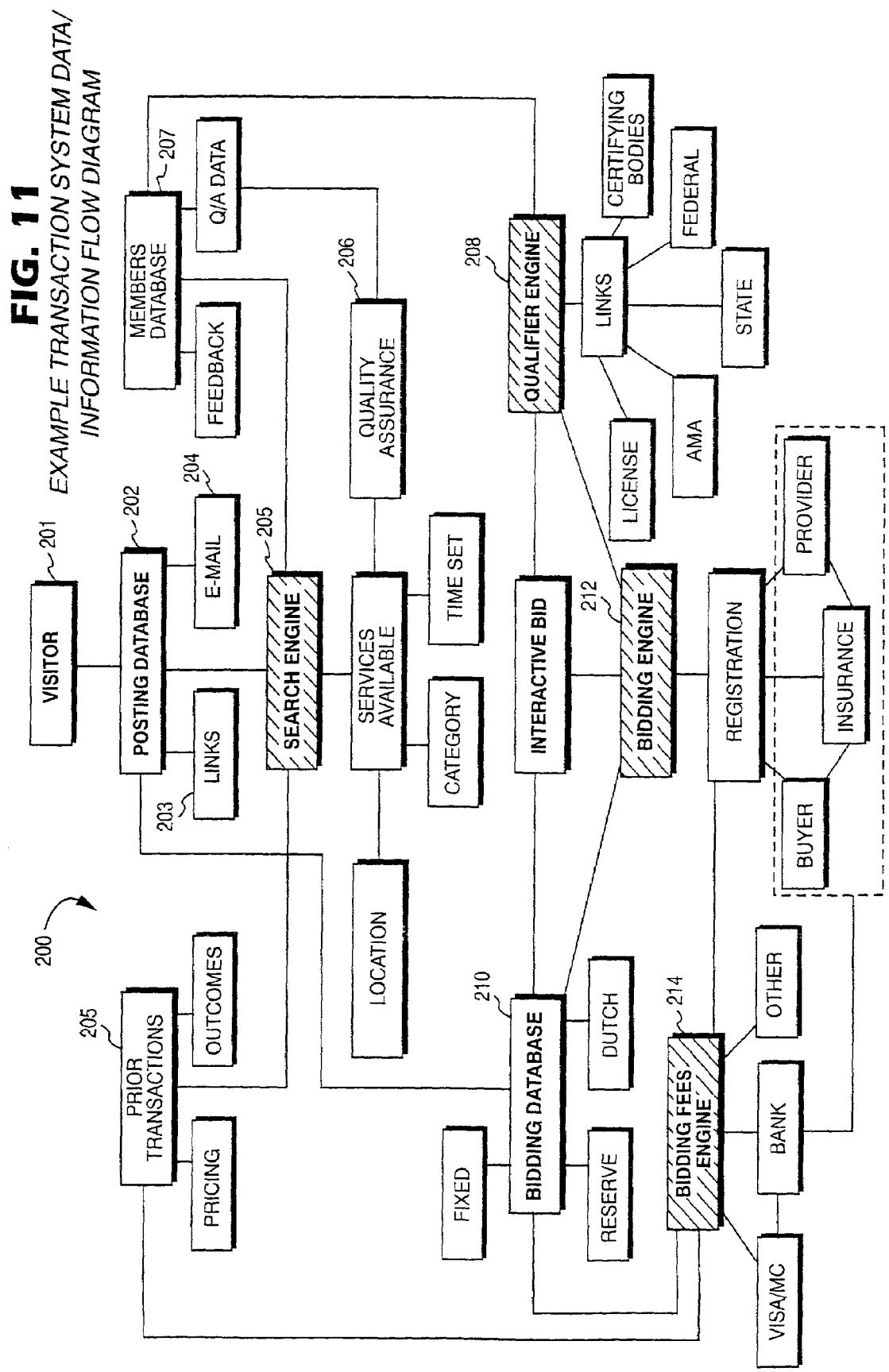
FIG. 11 EXAMPLE TRANSACTION SYSTEM DATA/INFORMATION FLOW DIAGRAM

| Home | Browse | Search | Sell Item | Registration | Help! |

=MedicalBid.com

Welcome, to the medical resource site, giving you a choice in your medical care!

*Bidding is as easy as one, two, three!*

One: Choose a medical category and/or type in a keyword search
Two: Optional, select a state of desired service.
Three: Optional, select a month you would like this medical service rendered.
Finally Hit the submit button.

Available services and provider qualifications will be listed for your bidding consideration.

Experimental Treatments/Studies

This is a ... area where qualified studies in progress are listed by investigators. The study protocols, subject selection, investigator qualifications, and regulatory approvals are listed when available Eye Surgery-$1500
Breasts Enlargement-$1100
Teeth bleaching-$50
Prescription drugs-all %50 off
Hospital bed-$999 kidney-$1000
prosthetic arm-$500
braces-$750
Nurse-$400/wk
eye-glasses-$75

Charity Begins Here!

Step #1
Service

- [ ] Allergy & Immunology
- [ ] Anesthesiology
- [ ] Cardiology
- [ ] Dermatology
- [ ] Endocrinology
- [ ] Family Practice
- [ ] Gastroenterology
- [ ] Geriatrics
- [ ] Infectious Disease
- [ ] Internal Medicine
- [ ] Medical Genetics
- [ ] Nephrology
- [ ] Neurological Surgery
- [ ] Neurology
- [ ] Obstetrics & Gynecology
- [ ] Oncology (Cancer)
- [ ] Ophthalmology
- [ ] Otolaryngology
- [ ] Pathology
- [ ] Pediatrics
- [ ] Physical Medicine
- [ ] Plastic Surgery
- [ ] Preventive Medicine
- [ ] Psychiatry
- [ ] Radiology
- [ ] Surgery
- [ ] Urology Eye Care
- [ ] Glasses/Contacts
- [ ] Eye Surgery/Laser Alternative
- [ ] Biofeedback
- [ ] Hypnotherapy
- [ ] Chiropractic
- [ ] Acupuncture
- [ ] Dietary
- [ ] Massage therapy
- [ ] Family Counseling
- [ ] Misc.

Supplies

- [ ] Equipment
- [ ] Health Products
- [ ] Beauty Products
- [ ] Prosthetics
- [ ] Supplies/Disposables

- [ ] Dental/Elective
- [ ] Dental/Cosmetic
- [ ] Oral Surgery
- [ ] Orthodontia

- [ ] Prescription Rx
- [ ] Non Prescription

Step #2(optional)
Select a state for Service:
--select--

Step #3(optional)
Select a month for Service:
--select--

Final Step: Submit or you may do a search by Keyword here

Keyword Search

FIG. 12
*EXAMPLE MENU PAGE*

FIG. 13
EXAMPLE REGISTRATION/SIGN-IN PAGE

| | Registration/User | |
|---|---|---|
| | Home \| Browse \| Search \| List Ad \| Registration \| Help! | |

EMedicalBid.com

*Welcome, to the medical resource site, giving you a choice in your medical care!*

Please fill out the following form. * Indicates a mandatory field.

Contact Information

| | |
|---|---|
| Name* | |
| Firm Name | |
| Street Address* | |
| City* | |
| State* | Please input a state or province, using an abbreviation if appropiate, ie NY etc... |
| Zip Code* | |
| Country | |
| Office Telephone Number | |
| E-mail address* | |
| Name of Contact Person* | |

Billing Information

| | |
|---|---|
| Card Type* | |
| Name on Card* | |
| Account Number* | 0000-0000-0000-0000 |
| Expire Date* | |

User Information

FIG. 14

*EXAMPLE USER REGISTRATION PAGE*

| | | |
|---|---|---|
| | Home  Browse  Search  Sell Item  Registration  Help! | |

EMedicalBid.com

*Welcome, to the medical resource site, giving you a choice in your medical care!*

Sell Your Item/Service

Please fill out the following form. Need help to get started, start here

* New to Selling?   * Seller Tips   * Fees   * Registration
* Medical Provider Registration   * Finding a Category

Contact Information

| | |
|---|---|
| Your User ID: | You can also use your email address |
| Your Password: | Forgot your password? |
| Name | |
| Firm Name | |
| Street Address* | |
| City* | |
| State* | Please input a state or province, using an abbreviation if appropriate, i e NY etc... |
| Zip Code* | |
| Country | |
| Office Telephone Number | |
| E-mail address* | |
| Name of Contact Person* | |

Billing Information

| | |
|---|---|
| Card Type* | |
| Name on Card* | |
| Account Number* | 0000-0000-0000-0000 |

FIG. 15A

*EXAMPLE SERVICE PROVIDER'S PLACE AD PAGE*

Expire Date*  [ ] [ ]

AD Information

Title required* [ ]
(45 Characters max; no HTML tags, asterisks, or quotes as they interfere with search) *see tips.*

Category required
You have chosen category # [ ]

Just click in the boxes below from left to right until you have found the appropriate catagory for your item. The chosen category number will appears in the small box to indicate that you have made a valid selection.

| Services | Supplies/Equipment | Alternative |
|---|---|---|
| Surgical | Equipment | Acupuncture |
| Urology | Buy | Chiropractor |
| Plastic/Cosmetic | Rent/Lease | Massage Therapy |
| Cardiac | Sell | Dietitians |
| Orthopedic | Supplies | Infertility Treatment |
| Podiatrists | Medication | Dermatology |
| General Medical | OTC | Chemical Rehab |
| Psychiatric | Cosmetic | Disability Services |

| Dentist | Optometrist | Charity |
|---|---|---|
| Cosmetic | Glasses/Contacts | |
| Laser Whitening | Eye Surgery/laser | |

Description * [ ]

You can use basic HTML tags to spruce up your listing.
You can add one primary photo, in the following format:
<img src=http:www.anywhere.com/mypicture.jpg> *See tips*

Web site/URL [http //]

Flat Rate Services

FIG. 15B

*EXAMPLE SERVICE PROVIDER'S PLACE AD PAGE*

Make your item stand out and get more bids! Try these options

Boldface Title?     $2.00 charge

Featured?     $39.00 *learn more*

Feature in Category?     $12.00 charge *learn more*

User Information

| | |
|---|---|
| Item/Service Location | [ ]<br>City, Region (e.g., Phoenix, AZ)<br>*More about regional selling*<br>Increase your exposure for no additional cost! when you choose a region, bidders will see your item on both the EMedicalBid and the Regional pages. |
| Payment Methods Choose all that you will accept | Money Order/Cashiers Check    Personal Check<br>Visa/Master Card    COD (Cash on Delivery)<br>Discover    American Express    Other |
| Where will you ship? | Will ship to United States only<br>Will ship internationally (worldwide) |
| Who pays for shipping? | Seller Pays Shipping<br>Buyer Pays Fixed Amount<br>Buyer Pays Actual Shipping cost |
| Other Expenses | Airline/Hotel cost included<br>Airline/Hotel paid by buyer<br>Lab work cost included<br>Lab work paid by buyer |
| Terms | 10% due, balance upon service received<br>20% due, balance upon service received<br>30% due, balance upon service received<br>50% due, balance upon service received<br>100% due after bid is accepted<br>Other, arrangement will be made with bidder |

Quantity [ ]

If quantity is more than one, then you will have a *Dutch Auction Item, see tips*

FIG. 15C

*EXAMPLE SERVICE PROVIDER'S PLACE AD PAGE*

Minimum bid [　　] per item
(e.g., 2.00) Please do not include commas or currency symbols, such as $.)

Duration [　　] days

Reserve Bid [　　] per item
(e.g., 2.00) Please do not include commas or currency symbols, such as $.) If the reserve bid price is not reached you are under no obligation to provide/sell service *(learn more).*

Minimum bid increment [　　] (e.g., 2.00) Please do not include commas or currency symbols, such as $.)

Pricing Adjustment in terms of medical condition:

Medical Concurrent Complexity Rating: *(Service provider submits this info)*

[ 0 ] No Concurrent Medical Problems That Would Impact This Service Complexity
[ 1 ] Some Concurrent Medical Problem/Condition That Impacts The Service Complexity
[ 2 ] Concurrent medical Problems And History of Prior Treatments That Affect the Complexity Of This Service

[ 0 ] No Medical Problem:    – 0% Adjustment From Bid Price

[　　]

[ 1 ] Some Medical Problems that will impact service complexity:

0%
10%
20%
30%

[ 2 ] Has a history or prior treatment/history that will affect the complexity of this service:

0%
10%
:
50%

Please press the "review" button below to see what fees are due immediately and what may be due if your item sells. You will not incur any fees until you accept the terms disclosed in the next screen.

Press [Review]                                    Looks good, place my listing [Submit]

Press [Reset] to clear the form and start over.

FIG. 15D
*EXAMPLE PLACE AD PAGE*

| | Home | Browse | Search | List Ad | Registration | Help! |

EMedicalBid.com

*Welcome, to the medical resource site, giving you a choice in your medical care!*

Plastic Surgery

| Select a *Month* for Service: | Select a *State* for Service: | KeyWord Search: [          ]  Submit  Reset |
|---|---|---|

| Plastic Surgery *HotItems!* | Time Left | Last Bid |
|---|---|---|
| Facelift, cheek or chin implants, CT, anytime, 5500. | 6hrs | 5525. |
| Neck Lift, get rid of that waddle under your neck, | 12 days | 1800. |
| Plastic/Cosmetic Surgery: | | |
| Lip Enhancement | 5day | 900 |
| Botox between eyebrows | 22hours | 325 |
| Plastic Surgery Wanted: | | |
| Nose reconstruction/May/NYC/ 2800 | 15days | 0 |

FIG. 16
*EXAMPLE SEARCH ITEM PAGE*

*EXAMPLE BIDDING FORM PAGE*

Your User ID

*Special Requirements:*

1. No medical contradiction
2. Procedure is appropriate for the bidder and discussed during a complimentary preoperative consultation
3. Facility fees, anesthesia fees, transportation fees are not included
4. Procedure will be performed at private surgical suite within a university affiliated hospital or one of the Yale affiliated hospital in Connecticut
5. Procedure can be scheduled for any month suited to meet your need.

*Each individual is unique. The result of a good surgery creates a natural look never a made up look. Improvement will vary from patient to patient depending on skin, age, and ethnic background.*

*To achieve optimal results sometimes several procedures may be needed in combination; this will be discussed during your complimentary consultation.*

*Payment: Ten percent of bid within five days of bid closure. The remaining monies are due two weeks prior to procedure schedule date.*

*Suitability: The seller of this service reserves the right to evaluate the bidder medically and aesthetically and if the procedure is deemed unsuitable, the monies will be fully refunded.*

For a better sense of the results from this procedure visit our web site at:
http://www.plasticsurgeon4u.com Indexing Words: Plastic surgery, Cosmetic surgery, Rejuvenation, beauty, Anti-Aging, Neck lift, Face lift, Lip enhancement, Botox, Liposuction, Nasal Reconstruction, Skin Resurfacing Cheek implants, Chin implants, Eye lift

FIG. 17B
EXAMPLE BIDDING FORM PAGE

BidderFeedback

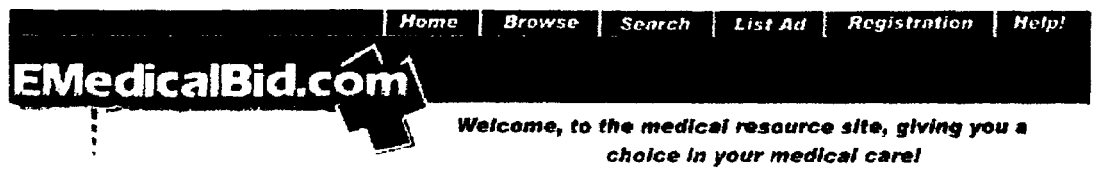

Welcome, to the medical resource site, giving you a choice in your medical care!

Bidder Feedback Form: (Describe Your Provider)

Provider:

Name: [        ]

License Number: [        ] [this will pop up after name is typed in]

Service ID Number: [This will pop up after name is typed in]

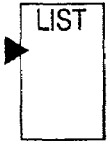

Service Category: [        ] ▶ LIST

Transaction Ease: [        ] ▶ 0 - Smooth
1 - Some delays things got done
2 - Difficult office problems getting things done Treatment Outcome: [        ] ▶ 0 - Smooth
1 - Some complications within scope of service
2 - Unexpected problems/ complications Suggestions/Comments About or For Provider:

[        ]

(160 Characters)

[Submit Form] [Reset Form]

FIG. 18

*EXAMPLE BIDDER FEEDBACK FORM PAGE*

Provider Feedback Form: (describe your patient)

Patient ID No. _____

Patient Compliance:

[Submit Form] [Reset Form]

*EXAMPLE SERVICE PROVIDER FEEDBACK FORM PAGE*

METHOD AND SYSTEM FOR PROVISION AND ACQUISITION OF MEDICAL SERVICES AND PRODUCTS

RELATED APPLICATIONS

This application claims the benefit of the following U.S. Provisional Applications, the entire content of each of which is hereby incorporated by reference into this application:

(1) "Method and System for the Provision of Medical Services" to Julian L. Henley, Ser. No. 60/186,542, filed Mar. 2, 2000;
(2) "Method and Apparatus for the Provision of Medical Services" to Julian L. Henley, Ser. No. 60/201,021, filed May 1, 2000; and
(3) "Medical Transaction Overview" to Julian L. Henley, Ser. No. 60/222,648, filed Aug. 3, 2000.

BACKGROUND OF THE INVENTION

1. Field of the Invention

The present invention generally relates to a business model method and apparatus for reducing transactional costs and/or facilitating improved choice in access times, locations and providers of professional services such as medical services and products. In general, the present invention relates to a method and system for implementing an electronic auction of medical services and products via the Internet.

2. Related Art

During the advent of a booming e-commerce over the Internet, many people have become familiar with the flexibility and cost effectiveness of shopping "online" for various goods via the use of Internet sites that offer public auctioning forums of one sort or another where sellers and buyers may participate in some form of interactive bidding process. However, while online auctioning has been employed somewhat successfully in the context of bartering for various products, problems arise when trying to accommodate the need for assessing professional service provider qualifications, scheduling, location and quality. One of the problems confronting an online bidder for professional services is that there is no readily convenient means for verifying the qualifications of an otherwise unknown service provider or for assessing the quality of services likely to be rendered by a particular provider.

Online auction systems for some types of medical practices have already been attempted. For example, U.S. Pat. No. 6,006,191—DiRienzo (1999) discloses a system where certain remotely accessible physicians' services are auctioned so as to better distribute the availability/utilization of those services across geographic/time domains. DiRienzo is specifically directed toward the reading of radiological and other medical images (i.e., image-reading diagnostic services). In this context, DiRienzo generally teaches:

"... The essence of the invention is the use of a decentralized, i.e., self-organizing, distribution system combined with bid queues to establish a market place which allows for continuously negotiated prices with control (over who reads the images, when they are read and what the fee will be for such a reading) being totally in the hands of the patient/gate keeper and the diagnostic physician." [column 8, lines 31-37].

Additional prior art patents of possible interest include:
U.S. Pat. No. 5,918,208—Javitt (1999)
U.S. Pat. No. 5,964,700—Tallman et al (1999)
U.S. Pat. No. 5,995,939—Berman et al (1999)
U.S. Pat. No. 6,014,629—DeBruin-Ashton (2000)
U.S. Pat. No. 6,035,288—Solomon (2000)

Javitt is directed to a system that allows a doctor to forecast utilization of services. Tallman et al discloses an online system that allows an insurance company member to select the most appropriate doctor. Berman et al teaches an e-mail system between doctors and others involved in a specific patient's health care. DeBruin-Ashton teaches a method of compiling a customized directory of medical service providers for a particular patient. Solomon is generally directed to online bidding for a service (i.e., any service, medical or otherwise) in which the price can be negotiated.

More recently, an Internet "web"-site, having a URL (uniform resource locator) address of "HealthMarket.com", has begun providing an online exchange for locating and comparing prices of proffered health care services/physicians. This web accessible facility purports to provide "an internet-based utility that allows employers, individuals, brokers and insurers to find, evaluate, purchase and finance healthcare insurance", and does not currently suggest or support online auctioning of personal medical services or products. Of course there are also the well known E-bay, Priceline.com, etc. online auctions and reverse bidding systems that are already well known.

SUMMARY OF THE INVENTION

This invention provides the flexibility of an improved online auctioning process for negotiating a price for the performance of personal professional services such as, for example, services performed by a physician on a patient (e.g., as opposed to remotely rendered impersonal services such as the reading of a medical image). In the context of providing such personal physical services, it would also be desirable to provide a convenient mechanism for a prospective bidder to verify that a selected service provider is properly qualified to perform an offered service and for informing the bidder as to the likely quality of the service to be provided at a particular time, location and price.

Another problem that arises within the context of providing an online auction forum for personal professional medical services is that a medical service provider has no convenient way to assess the medical history or physical condition of a prospective patient. Since the extent and cost of treating a particular patient may depend upon the patient's medical history, it is difficult for a provider to fix an offering price on a service. Consequently, one feature of the present invention allows medical service providers to assess the physical condition and medical history of a prospective patient. In addition, the invention provides a fair and symmetric mechanism that accommodates errors made in the appropriateness of rendering a particular medical service/procedure without a full knowledge of a patient's pre-existing medical condition.

The present invention also introduces helpful transaction evaluation features such as an associated "complexity rating" for a particular service/procedure and a "complexity divergence" indicator which provides an indication of the degree that a particular service/procedure may ultimately differ (e.g., due to unforeseeable complications or severity of the treated condition) from the conventional known complexity associated with that service/procedure. Such features can serve to prevent various privacy issues that might arise during such transactions from encumbering the bidding process and can make the overall transaction more equitable. For example, the bidding process may be made contingent on the medical appropriateness of the actually rendered service and the amount ultimately to be paid on a winning after bid may be varied based on a complexity rating for the procedure and the complexity divergence score attributed to a particular patient. In this manner, the moral, ethical and legal obligations of a medical practitioner/provider may be met and the mutual bidder/seller's interests fully protected.

This invention also may provide the flexibility of an online auctioning process for other professional services such as, for example, legal or financial services.

In the context of obtaining personal medical services, for example, people who are uninsured or only partially covered by an insurance policy are provided a more convenient mechanism for identifying and contacting a high quality, qualified medical service provider that will provide a desired medical service at the desired quality, time, location and price. Medical service providers who own or operate medical facilities for performing such services are often willing to reduce fees if it would enable them to keep the staff and resources of their facility from being underutilized. For example, during slow or inactive periods, the under utilization of facility and staff reduces profitability and thereby drives up costs for conventionally scheduled patients.

This invention provides a mechanism whereby a patient, an agent acting on a patient's behalf or an insurance company can identify an underutilized facility thus enables the insurance company to negotiate a lower price for the policyholder. An uninsured patient may also secure the services at a more favorable price by agreeing to have the desired medical service performed during a period of what is otherwise expected to be facility underutilization. Such facilities and providers also may agree to lower pricing if they receive payment at time of bid closure instead of, for example, after a customary 8-12 week post-service insurance reimbursement delay.

Subject to certain restrictions, such as the availability of an otherwise underutilized medical facility in reasonable geographic proximity to the patient, a novel type of medical insurance policy may be offered wherein the policyholder agrees to have a desired medical procedure or service performed at an otherwise underutilized facility at "market value." The cost for such a "market value" policy can be reduced because the insurer may be able to negotiate a lower price for securing a needed service on a case-by-case basis (e.g., by contracting to have a service performed at a particular time, or within a specified range of times, in an otherwise underutilized facility).

Alternatively, a novel lower-cost lifetime (or shorter period) maximum benefit insurance package could be offered in such a market (i.e., such as that introduced by the present invention). For example, the premium rate for such an insurance policy could be set proportional or inversely proportional to the residual benefit in either a linear or a non-linear fashion.

Alternatively still, a novel insurance package could be provided in which health and death benefits are combined together. In accordance with one such contemplated example insurance package arrangement, the accrued death benefit of the policy (e.g., using the standard life insurance policy model) can be used to bid for health benefit services to preserve life. The expense (e.g., finalized bid price) of the rendered medical services is taken from the policy residual death benefit and the policy holder's death benefit then becomes the remaining balance. This creates a situation of finite resources that will impose market forces on health providers where each consumer strives to get the best quality for the best price and preserve the remaining benefit for themselves and their families. The individual again is empowered to make those critical heath care decisions and impose market forces on existing providers by means of this device and method.

Typically, facilities providing medical services, particularly elective procedures, spend a significant portion of their operating budget on advertising and promotion. An important purpose of the advertising is to assure that the facility is fully utilized. This invention provides other means for assuring efficient facility utilization. Thus, even if medical services were to be provided at a reduced price, the savings realized by reduced advertising and promotion now can be shared with the patient, thereby reducing overall medical costs for the consumer and increasing profitability for the medical service provider. This invention provides a method and apparatus that will enable prospective patients to easily identify and access an otherwise underutilized medical facility to negotiate a favorable fee for services subject to scheduling restrictions and other "specifications" set by the medical service provider. Likewise, underutilized medical facilities may now offer services at a negotiable fee in order to more fully utilize the resources of the facility.

Conventionally, most medical services are sold under a fixed-price protocol whereby the medical service provider sets a price for the service and a patient either accepts or rejects the price. The time, and sometimes the place, that the services are rendered in accordance with this protocol may be regarded as "flexible" in the sense that a medical service provider will typically establish a time and place (i.e., specifications) for rendering the service that is mutually acceptable to the parties. However, alternative protocols for perfecting buy-sell transactions between patients and medical service providers that are responsive to market forces, such as, for example, an auction or an exchange for buying or selling medical services similar to a stock exchange, have not been traditionally available.

Market research has indicated that people, lacking insurance for reimbursement of drug costs, typically pay as much as 15% more for a prescription medicine than people having such insurance for the same medicine. For example, seniors without drug coverage may not only lack insurance to protect against high costs, but may not have access to discounts and rebates that insured people receive. Uninsured persons may not purchase a needed prescription medicine simply because they cannot afford it. Moreover, market research indicates that spending for prescription drugs is currently growing at a rate that is twice that of other types of healthcare expenditures. This perceived inequity in pricing between insured and uninsured prescription medicine buyers now may be diminished by this invention providing a marketing system and method that enables the uninsured to buy prescription medicines at a "fair market price" that is both dynamic and determined as a result of competitive market forces. For example, overstocked medications that are to expire in 6 months may be sold at half price to those patients that can use them immediately.

This invention more efficiently schedules personal physician procedures during known predictable slow times (for instance during the night) so as to better match medical resources with medical needs across geographic/time domains. For example, this invention can provide an automated system where a doctor is enabled to accept certain bid/cost proposals for his/her services and then decide whether to accept or decline the bid price (thus more efficiently and economically distributing medical services to desiring patients that might pay a lower cost because the procedure would be done during "off" hours or the like).

The present invention may use a client computer system or suitable handheld wireless device comprising a telecommunications link to a remote medical transaction server via a digital communications network, such as the Internet, for enabling prospective buyers of medical services to negotiate with providers of medical services to identify and secure a reduced market-driven price for desired medical services. If desired, a condition may be imposed so that that the services will be rendered by the facility during a period of what would otherwise be facility underutilization.

This invention may also use a medical transaction system comprising telecommunication links to a digital communications network, such as the Internet, that enables a plurality of prospective sellers of medical services to offer medical services to patients, insurers, and other third parties using an auction format. A minimum reserve price may be established for bids received using an auction format.

A buyer and seller of medical services can also communicate with each other to establish a mutually acceptable fee for services, the mutually acceptable fee being subject to a medical evaluation and restriction regarding the time and place where the medical services will be provided. Options may be provided in choosing a less convenient time and place for receiving medical services in exchange for a better price for his/her needed medical services. The qualifications of a medical service provider for the provision of an offered medical service may be authenticated. In fact a buyer and seller of medical services may have access to each other's respective transaction history and feedback history.

The present invention may provide an online business method and system whereby medical services and supplies (e.g., prescription medicines) are offered for sale in an auction forum subject to selected conditions that can be specified by a medical service provider such as, for example, the time and/or place where the personal medical service is to be rendered.

In addition, the invention may enable patients, whether insured or uninsured, to acquire elective surgical services, chronic rehabilitation services, medical equipment support, and other non-emergency medical and dental services through an auction format bidding process. Various covered and non-covered services such as podiatry, chiropractic, acupuncture, homeopathic, behavioral modification treatment and therapy, weight loss, hypnotherapy and other health related services may also be included for online listing and bidding in an auction format using the method and system of the present invention. Although many medically-related health services and products are subject to regulation to assure quality, the establishment of specific qualifying conditions and quality control measures may be implemented by the system of the present invention.

An efficient arrangement is also provided for online solicitation of consumer feedback information from patients which, after being acquired, is maintained in a transaction database and made accessible to other prospective patients. The convenience of online availability of a consumer feedback database to prospective patients and other buyers of medical services should ultimately serve to improve the quality of medical services provided to patients.

A person desiring a specific medical service can be provided with a means to identify a medical facility offering such services and can negotiate obtaining the services at a "preferred" price in return for agreeing to receive the services during a period of otherwise expected facility underutilization. A further feature of the present invention allows a "standby" option to be implemented wherein the performance of services are provided at a reduced rate to a buyer willing to accept treatment on a "standby" or delayed basis. This feature may be particularly beneficial in that it provides a further component of cost reduction to the patient and/or his/her insurer and could provide the medical provider with greater assurance that revenue is not lost. Using the bidding/auction-type format of the present invention, payment (either partial or full) may be made or secured electronically at the time a bid is accepted (rather than the customary 8-12 weeks after provision of a service, a basketful of paperwork and a plurality of phone calls).

A practical market-driven system that permits efficient buying and selling of medical services should also be subject to both strict quality control and acceptable practices by the medical community. Consequently, another aspect of the present invention is that a medical service provider's qualifications are preferably authenticated/verified using an authentication engine prior to posting either a global or local offer to sell a service. In addition, an offer-acceptance agreement between a medical service provider and a patient may also be optionally qualified by a restriction that a patient submit to a medical evaluation to establish the appropriateness of the medical service for the particular patient.

Yet another feature of the present invention enables a qualified buyer of prescription medicine and non-prescription medicine to post a proposal to buy the medicine at a price that he/she is willing to pay for the medicine via a public database accessible to sellers of the medicine and to receive and communicate offers to sell the medicine at the seller's proposed purchase price.

Direct links to transaction feedback databases can be established to allow consumers of medical services to verify and evaluate a particular provider's product or service. The present invention also allows an agreement between a patient and a medical service provider to be conditioned on establishing the medical fitness of a patient for receiving a particular medical service.

In general, the invention provides an efficient apparatus and method for exerting market forces on the cost of delivering medical services and for streamlining potentially costly administrative procedures.

BRIEF DESCRIPTION OF THE DRAWINGS

These and other features and advantages provided by the invention will be better and more completely understood by referring to the following detailed description of presently preferred embodiments in conjunction with the drawings, of which:

FIG. 3 is a chart illustrating an exemplary revenue forecast/projection based upon data as extrapolated from a service facility's historical revenue databases;

FIG. 4 is a table that illustrates exemplary standard procedure pricing employed by a medical service facility offering plastic and reconstructive surgical procedures;

FIG. 11 is an block diagram illustrating example functional processes available to a web-site visitor upon accessing online the medical transaction system of the present invention;

FIG. 12 is a bitmapped image screenshot of an example proffered services menu web page provided online to a prospective bidder;

FIG. 13 is a bitmapped image screenshot of an example user log-in web page provided online for registered users of the transaction system of the present invention;

FIG. 14 is a bitmapped image screenshot of an example registration form web page provided online to prospective uses of the transaction system of the present invention;

FIGS. 15A-15D are a bitmapped image screenshots of an example "Place-ad" form web page provided online to a service provider;

FIG. 16 is a bitmapped image screenshot of an example user "Searchitem" web page provided online to a prospective bidder;

FIGS. 17A and 17B is a bitmapped image screenshot of an example bidding form web page provided online to a registered bidder;

FIG. 18 is a bitmapped image screenshot of an example Bidder Feedback form web page provided to an online registered bidder.

DETAILED DESCRIPTION OF EXEMPLARY EMBODIMENTS OF THE INVENTION

Figure 1:
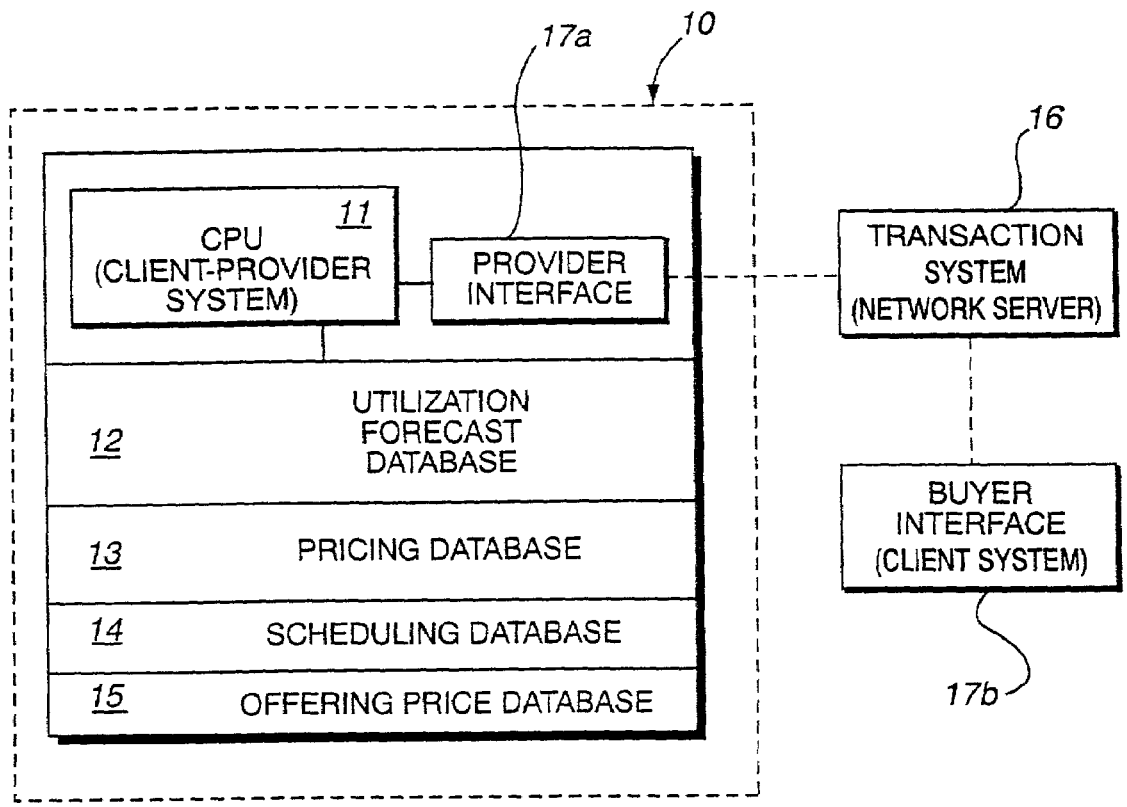
FIG. 1 is a block diagram illustrating an example of a client server/scheduling system that may be used by a medical service provider in accordance with the medical transaction system of the present invention.

FIG. 1 illustrates an exemplary client-provider computer system (10) for use, for example, by a medical service provider that enables a service provider to schedule facility utilization and to automatically compute an offering price which may be made dependent upon factors such as the temporal availability of facility resources and personnel.

In this example, client-provider server 10 includes at least one central processing unit (CPU) 11 and a plurality of data bases 12 through 15 maintained on one or more data storage devices. CPU 11 receives data from a facility utilization forecast database 12, a medical service standard pricing database 13 and a facility-maintained facility scheduling database 14. The CPU 11 receives data from the facility utilization forecast database 12 and the service standard pricing database 13 to compute a special offering price for services rendered during periods of facility underutilization. The computed special offering price is stored in an offering price database 15.

The CPU transfers data from the special offering price database 15 to interactive transaction system 16, for example, by means of a digital communications interface device 17a, such as a modem and associated telecommunication circuits. A prospective patient/buyer of medical services may likewise be connected to transaction system 16 via similar interface 17b. For the purpose of the present description, transferred data from the provider is collectively referred to as "specifications" of the offered service. In a preferred embodiment, this transferred data includes scheduling dates, at least one medical service being offered for sale and an offering price for the medical service.

Figure 2:
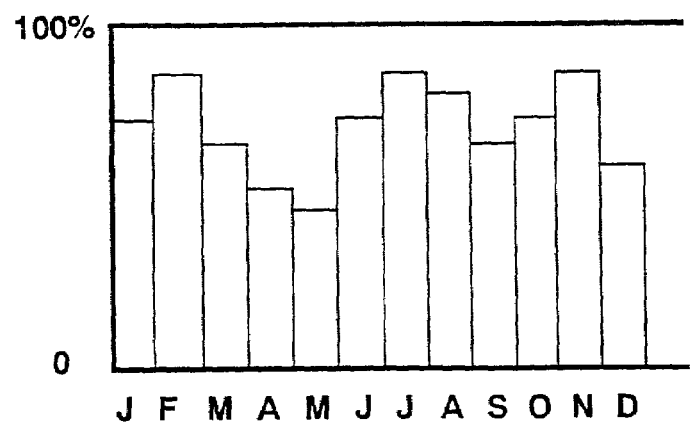
FIG. 2 is a bar graph illustrating an exemplary future facility utilization projection over a one year time period.

Specifications associated with a particular offered medical service may, for example, be determined by historical analysis of market behavior. FIG. 2 shows an exemplary graphical representation of projected utilization of a particular medical service facility based on historical use data. The percent utilization of facility resources is indicated along the ordinate for calendar month dates along the abscissa. In the example, certain months are seen to be more underutilized than others. Of course, the goal of an efficient medical service facility is 100% utilization of their resources during the entire year. Accordingly, it is to the medical service provider's advantage to schedule facility utilization, even at a reduced price, during the expected "low" utilization periods in order to at least partially offset operating costs of the facility. An increased number of patients/buyers of medical services may be attracted toward using the facility if the facility is willing to offer services at a special offering price during these otherwise expected low periods. The offering price for services that are scheduled for periods of greatest expected underutilization can be substantially reduced below a "standard" price in order to generate revenue to offset operating costs.

The historic average hourly revenue of a medical service facility, again using fictitious exemplary data, may be contained in a facility revenue forecast database such as that shown in FIG. 3. In this database, projected average hourly costs ($/HC) for operating the facility and projected average hourly facility revenue ($/HR) for each of the future months are stored. Projected net hourly income ($/HR-$/HC) for operation in future months is shown in column 3. In this example, eight of the twelve upcoming months indicate a loss in projected net hourly income. If the facility usage is increased during these "low" months, the net hourly revenue can be increased. The stored historic revenue data for the low months can be used to compute a special offering price for services to be rendered during the low months as will be discussed later.

Many medical service providers have a base pricing structure (e.g. a standardized base price or "BP") for a particular medical service which is, for example, related to the difficulty, attendant risk and time required for rendering the service. Also associated with various medical services may be certain overhead expenses, fixed costs, risk reduction costs, and disposable costs. An example of such a base pricing structure for a plastic surgery "surgicenter" is illustrated by the pricing table of in FIG. 4.

Figure 5:
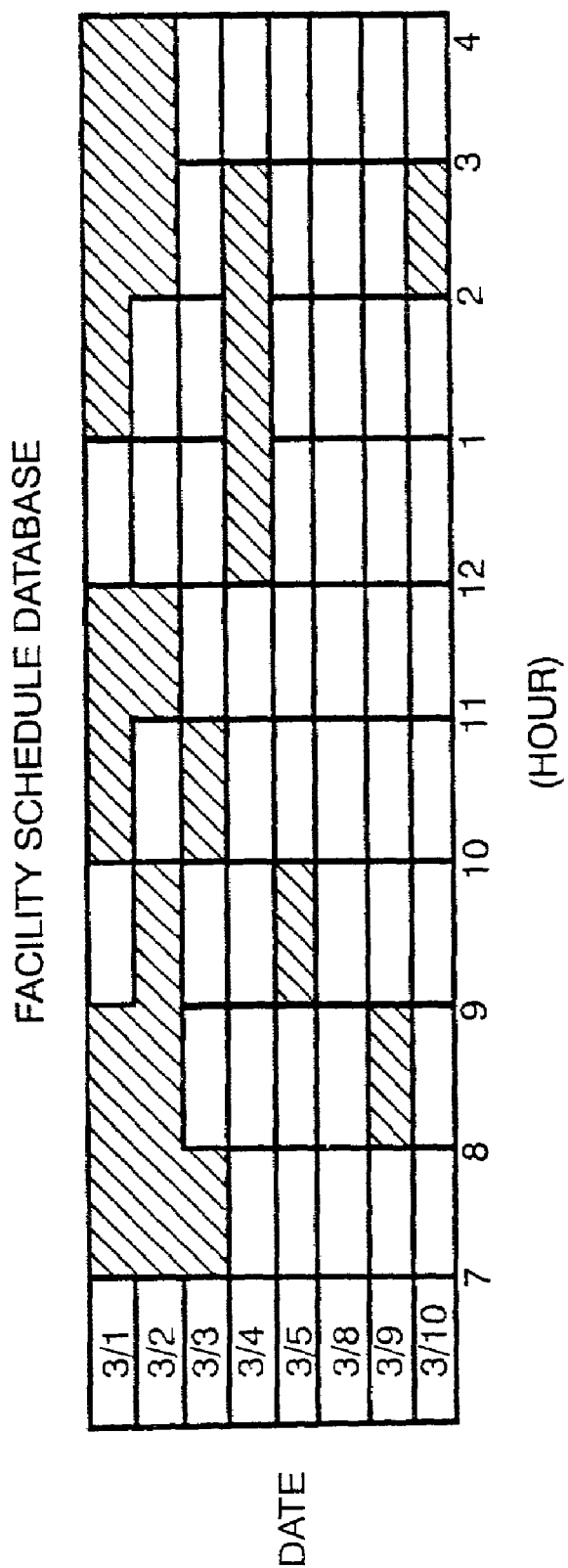
FIG. 5 is a table that illustrates an exemplary proffered service facility schedule for identifying periods of facility underutilization.

If a patient agrees to have one of the listed procedures performed at a time corresponding to a period of "low" utilization, the provider can offer a price reduction in consideration for the patient's flexibility in scheduling. As the facility schedule fills, the offering price of further offered services can be automatically adjusted upwardly in response to the degree of then-anticipated future underutilization. That is, data reflecting the scheduled utilization of the facility, as maintained in a facility schedule database illustrated by the chart at FIG. 5, can be constantly updated as patients purchase services at special offering prices. When the scheduled utilization exceeds the projected utilization for a particular time period, the special offering price can be selectively increased or decreased, in a manner that is sensitive and responsive to the demand for services.

A medical service provider may employ a customized algorithm, encoded and stored, for example, on a computer-readable medium, to compute a preferred offering price ("OP") for a particular medical procedure in a format that can be uploaded, on-line, onto the interactive transaction system 16 for posting and solicitation of registered buyers. For example, consider a board certified (i.e. qualified) plastic and reconstructive surgeon who is a registered medical service provider having an upcoming surgery schedule as illustrated by the hatched areas of the chart in FIG. 5. The surgeon wishes to schedule one of a plurality of medical services that he/she is qualified to provide during the currently unscheduled time. The surgeon has a base price, BP=$10,000, which is charged for performing a face lift which takes, on average, four hours. On the schedule shown in FIG. 5, the only possible dates available for performing the 4 hour procedure (without rescheduling other procedures) are 3/3, 3/4, 3/5, 3/8, 3/9 and 3/10. There are 54 hours available for scheduling during these dates (i.e. T=54 hours) of which 8 hours have been scheduled. The unscheduled time ("UT") available during these dates is 46 hours (i.e. UT=46 hours). An offering price ("OP") may be computed using a formula given by Equation 1 below:

$$OP = BP + UT/T(RP-BP) \quad \text{Equation (1)}$$

where "RP" is a reserve price for the procedure. That is to say that RP represents the minimum price that the surgeon is willing to accept for providing the face lift. The RP may, for example, be equal to or greater than the sum of the out of pocket costs, including the price of implants (if necessary), disposables, malpractice insurance and facility costs such as payroll and equipment leasing. Of course, Equation (1) is only one of many possible algorithms that may be used for computing an OP.

In the above example, using Equation (1), the preferred OP for the procedure is:

$$OP = \$10,000 + 46/54(\$5000 - \$10000) = \$5741 \quad \text{Equation (2)}$$

Figure 6:
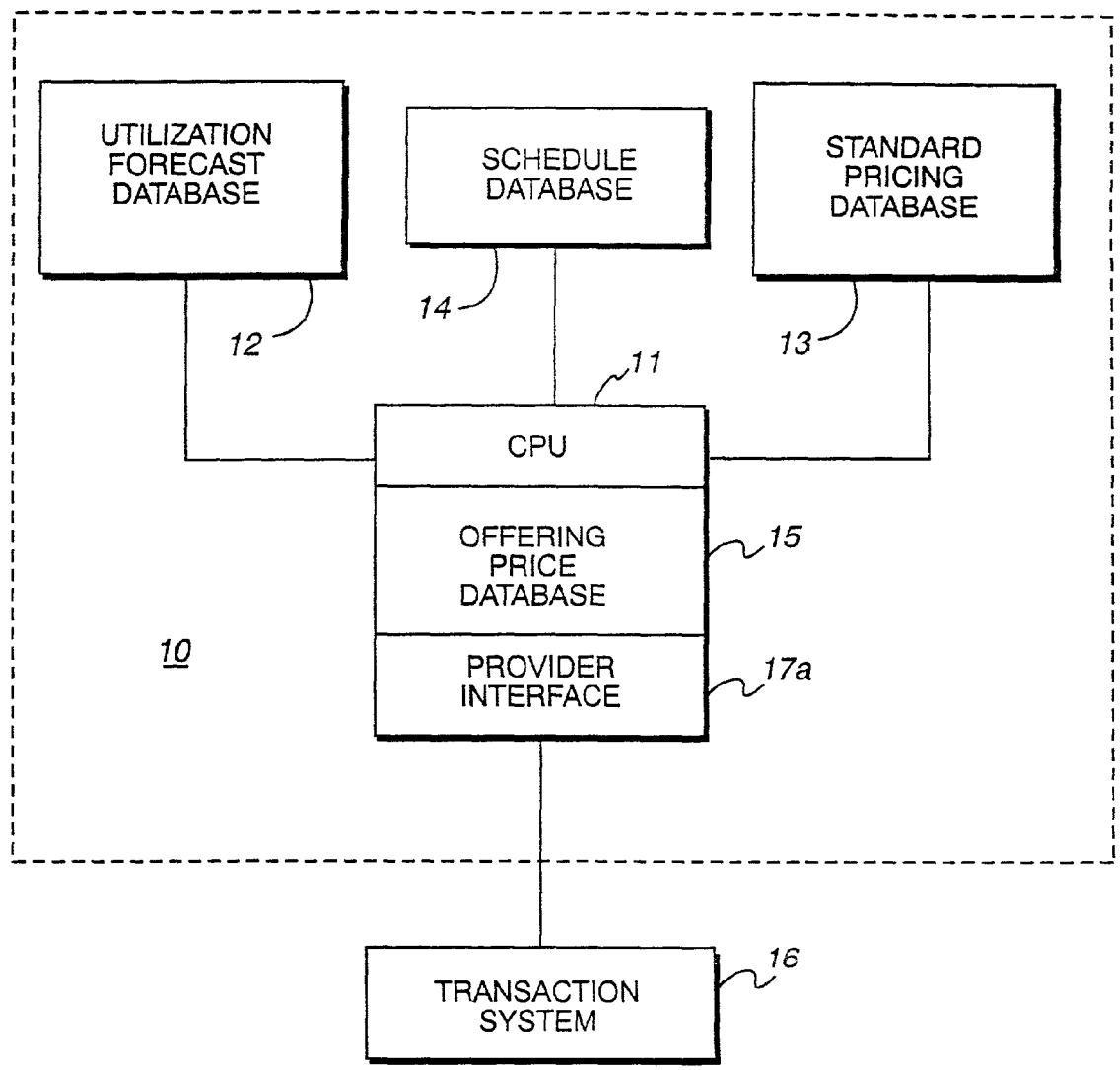
FIG. 6 is a block diagram illustrating an exemplary medical service facility computer system electronically connected to an interactive marketing system such as the medical transaction system of the present invention.

Thus, the surgeon may access transaction system 16 and post an offer to sell a face lift for $5741, with specifications (i.e. conditions precedent) attached thereto as follows:

Medical service ID: (system CPT code for face lift/Rhyditectomy)
Facility: Cedars of Sinai Outpatient Surgical Center
Location: Los Angeles, Calif.
Offering Price: $5741
Available Dates: 3/3-3/5/00 and 3/8-3/10/00
Payment: in full within 7 days of bid closure
Other requirements: lab work and medical evaluation prior to scheduled data of surgery FIG. 6 is a diagram illustrating an exemplary connection between a medical service provider and an interactive marketing system in accordance with the present invention. A medical service facility identifies periods of projected future underutilization using an in-house scheduling and pricing system 10, and offers medical services to prospective patients during these otherwise underutilized periods at a reduced price, wherein the reduction in price is directly related to the currently projected underutilization of the facility during the subject period. As discussed earlier, historical facility utilization data, contained in the utilization forecast database 12, is compared with the scheduling database 14, which contains already scheduled services for the relevant time period, and the percent of currently expected facility utilization computed for each upcoming date. The pricing database 13, containing a list of services and/or procedures, the time required for rendering each service and the base price for each service or procedure, is modified by a suitable algorithm via the CPU to generate a current offering price database 15. The offering price database contains a list of upcoming dates, a list of procedures and/or services and a special offering price for services rendered at the specified date. The algorithm used to adjust the base price of a service has, as an input, the percent utilization, and will preferably reduce the offering price when the percent utilization of the facility is low, and conversely, will be a factor in raising the offering price as the percent utilization rises.

The above description of a medical service provider's scheduling and pricing system 10 for generating preferred OP for services rendered during periods of low facility utilization, is not meant to be defining of all such systems but merely exemplary of one such system which may be used by a provider for structuring a preferred OP. The preferred OP is ultimately intended for posting on a global database, or interactive "bulletin board", that is reasonably accessible to a large number of prospective buyers. A system for receiving, organizing, qualifying and posting such specified medical services (and OP), which can be accessed by a plurality of buyers, as well as sellers, of such medical services is shown in FIG. 7.

Figure 7:
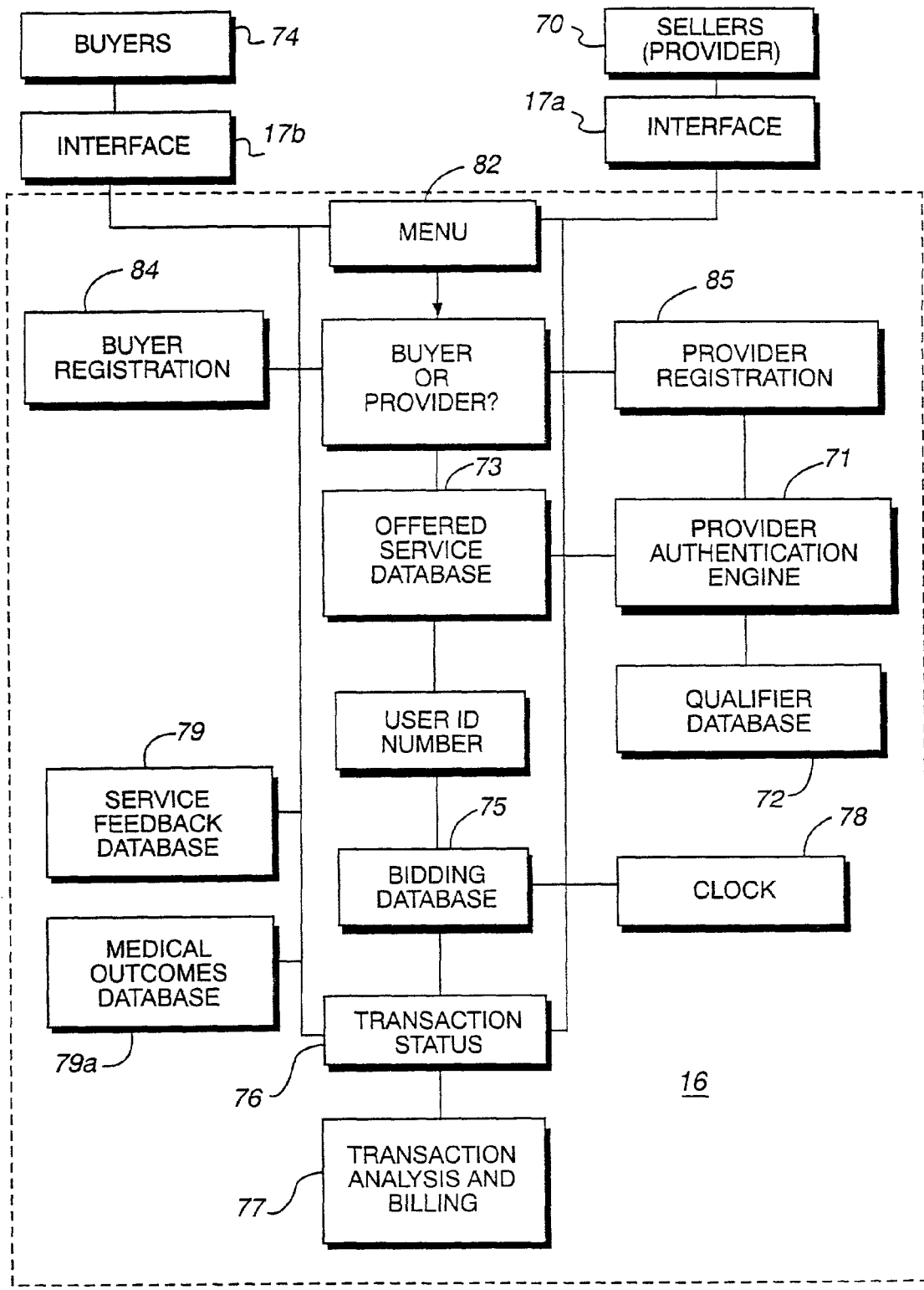
FIG. 7 is a block diagram illustrating an exemplary online marketing system for providing an interface between a medical service facility/provider and patients/bidders desiring to buy/bid upon such proffered medical services.

FIG. 7 is a block diagram illustrating an exemplary system that is operable for conducting a variety of types of buy-sell transactions between a medical service provider facility offering medical services for sale, and patients desiring to buy such medical services. Although the system 16 permits different types of buy-sell transactions to be conducted, as will be discussed later for the purpose of continuity, simplicity, and example, a single simple transaction will first be considered wherein a medical service provider offers a specified medical service for sale at a preferred price, and the offer is presented to a plurality of buyers and accepted by a single buyer.

With continuing reference to FIG. 7, a specified medical service and offering price, contained in the previously described offering price database 15 within the facility scheduling and pricing database system 10 (FIG. 1), is transmitted to a market access system 16 via a medical service provider-controlled interface 17a, such as a keyboard/CPU/modem/telecom circuit, or other computer networking device. Prior to posting the offer for sale, the system 16 prompts the provider (seller) 70 to enter a registration identifier. If the provider is not registered to offer services for sale on the system, the provider must register online. In order to register, the provider must identify himself/herself and enter one or more medical services that the provider is qualified to render. The provider's qualifications for performing the stated medical services are authenticated by means of a search engine 71 having a direct link to a qualifier database 72 and/or hyperlinks to one or more other qualifier databases 72.

The term "search engine", as used herein, means an apparatus (or method) automatically operable for receiving a user generated label, searching a directory comprised of one or more databases for a matching label and identifying databases within the directory which contain a matching label. The term "qualifier database," as used herein, means an electronically accessible computer-readable storage medium containing authentic certification data for medical service providers. Some examples of qualifier databases include the AMA's membership roster, a State Medical Licensing Board's roster of licensed physicians, the American College of Surgeons roster of board certified surgeons and a roster of Board Certified Plastic and Reconstructive Surgeons, as well as specific hospital staff privileges roster.

If the medical service provider is qualified to render the medical service being offered, the qualifications are authenticated by the system 16 and the provider-transmitted service and offering price data, including any restrictions (specifications) are accepted by the system 16 as a conditional offer for sale. Put another way, a statement of an intention to offer specified medical services for sale at a specified date and time, or range of dates and times, at a specified price is posted on an offered service database 73.

A plurality of patients 74 gain viewing access to the posted data via a patient interface 17a (e.g. via the Internet). If the conditional offer for sale is acceptable to a patient (or other buyer such as a patient's insurance company) who is a registered user of the system 16, the patient/buyer submits his/her offer to buy (bid) by on-line posting on a bidding database 75. If the offering price of the medical services, which offering price is included in the specifications of the offer to sell the medical service, is "fixed", that is, not open to negotiation, the bid is compared with the offering price and, if a match occurs the bid is accepted and the transaction recorded in a transaction status storage device 76. If the consumer demand for the service at the posted "fixed" price is greater than the number of services offered at the "fixed" price, other bidders can bid the price higher to gain priority for the limited service at the "fixed" price (Dutch Auction).

The system 16 notifies the buyer and seller that the transaction is complete and the registered buyer and seller identification and transaction selling price entered into a transaction analysis and billing database 77 wherein the parties to the transaction are billed for system use. The buyer and seller may then communicate directly in order to satisfy specifications posted by the provider such as scheduling a medical exam and arranging to have required lab work done prior to the time the medical service is to be rendered.

In the exemplary transaction presented above, the provider's offer to sell the medical service cannot be construed as an actual offer for sale because the facility's ability to render consideration is limited by the facility's scheduling capacity. In other words, thousands of patients viewing an offer to perform a rhinoplasty on Thursday, May 22, 2001, at 7:45 AM at a special price of $2500, cannot all be rendered consideration by the offering facility. Thus, the system 16 must be able to receive offers to buy a posted medical service in a serial manner to enable the medical service facility to accept only those offers for which it can reasonably expect to provide consideration, and reject buy offers received after 100% facility utilization is realized. Accordingly, a clock 78 records the time that an offer to buy is placed to prioritize such bids. Higher bids (i.e. bid purchase prices exceeding the "fixed" price) may receive priority over a lower, but otherwise acceptable, bid which is received earlier. After the medical service provider's facility schedule is full for specified dates and times, additional patients' buy offers (bids) are either rejected or may be accepted by the medical service provider on a "standby" basis for other future slots.

In any practical buy-sell system, whether market-driven or otherwise, the medical service provider must have the ability to bind a patient to a legal contract under the terms of the patient's offer to purchase. Similarly, the patient must have the ability to legally bind a medical service provider to the terms of the medical service provider's offer to sell. The system 16 may provide a registered prospective purchaser of medical services access to quality assurance data relating to the qualifications of the provider that are required in order to provide the particular medical service, such as, for example, statutory state and federal provider requirements, provider qualifications, hospital privileges and board certifications.

In the future, the data that is made available to prospective buyers of medical services may be enlarged to provide transaction outcomes history and other performance criteria about the provider as the data becomes available to the public via the system 16 or other Internet links. The availability of such additional transaction outcome historical data for a provider will allow the consumer of medical services to bid with confidence; being reasonably assured by the experience of others that he/she will be getting the "best quality for best price". In this respect the system provides the consumer with information that has not previously been readily accessible and/or verifiable. Most medical referrals are currently made by roster participation (lowest bidder). Provider selection is also typically made from neighborhood hearsay data, combined with such a list of qualified providers.

Figure 8:
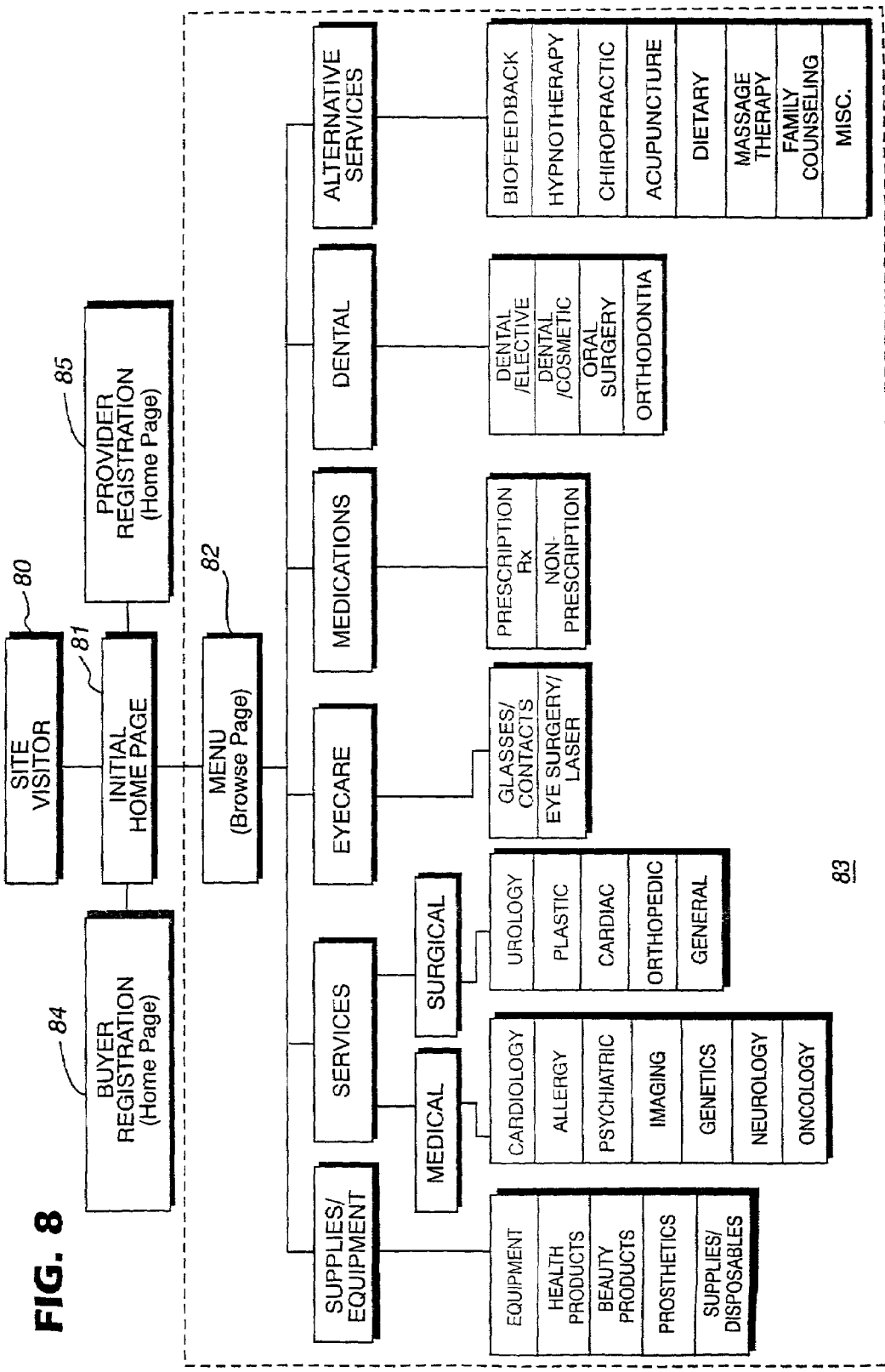
FIG. 8 illustrates an exemplary user interface of the medical transaction system of the present invention for enabling a buyer or seller of medical services to access the system and to interact with other users.

An example of a "home page" having an Internet identifier: "emedicalbid.com", useful for accessing and browsing the system 16 in accordance with the present invention, is depicted schematically in FIG. 8. A visitor 80, who may be either a prospective buyer or seller, is directed to the home page screen 81 and identifies himself/herself/themselves as either a buyer, a seller, or payor, (e.g. an insurer) of medical services/products, and provided with a menu 82 displaying a variety of medical related services and product options, including options for buying or selling medical services, medical equipment, and medical supplies such as drugs. The visitor 80 may browse the various menu-linked service databases 83 by choosing the desired category of services. If the visitor wishes to buy or sell a medical service, the visitor must first complete a registration process by completing a buyer registration questionnaire 84 or a provider registration questionnaire 85. The buyer of services may be similarly subjected to credit qualification to minimize "no show bids".

The term "medical services", as used herein, includes surgery, medicine, radiology, medical equipment sales or leasing, pharmacy, alternative medical services, dentistry and dental procedures, rehabilitation services and other medical services, the provision of which are subject to licensing. The method for selling a medical service in accordance with the present invention requires enrolling at least one, and preferably a plurality of, medical service provider(s) using an on-line registration system. After a medical service provider is enrolled, the medical service provider may request the system 16 to post an offer to sell a specified medical service included within the menu 82 of medical services at a specified offering price.

The system 16 authenticates the qualifications of the medical service provider by searching the qualifier database 72 (FIG. 7). The qualifier database 72 includes every service listed in the menu of medical services and the licensing requirements for providing the particular service. The qualifier database contains a list of medical services, the qualifying requirements for rendering such medical services, and hyperlinks to databases storing the identification of medical service providers having satisfied a particular qualifying requirement. If the provider's qualifications for performing a particular service have not been previously authenticated by the system, a software qualification engine will access and search external databases that identify qualified providers for the particular medical service.

In an example embodiment of the qualification engine of the present invention, a medical specialty Board Certification awarded to a given practitioner is used to define the cluster of CPT coded procedures that the practitioner may perform well. If a practitioner posts a procedure or service for bids for which he/she is not duly certified, an internal alert is raised by the qualification engine and a request for specific qualifications is made to practitioner. In this manner, the qualification engine prevents a cardiologist, for example, from posting a body liposuction as a procedure for soliciting bids. Moreover, the qualification engine may implement this and other predetermined restrictions using an evolving list of threshold qualifiers for accommodating orphan procedures practiced by the various medical specialties.

Once the qualifications are authenticated, an offer to sell the specified medical service and the specified offering price is posted on a global database 73 that is accessible, on-line, to a plurality of buyers. For posting purposes, the system uses a basic qualification threshold. It may be desirable to provide means for the patient to access additional provider qualification to bolster the bidder's comfort with placing a bid. The system will prevent a dentist from posting an offer to perform a liposuction procedure but will not prevent a general surgeon (legally qualified) from offering such services. A provider's membership in the American Liposuction Society will be reassuring to the prospective bidder but such membership will not define the gateway to performing such a procedure.

It is the purpose of the system to bring free market forces to healthcare while providing a quality assurance umbrella. It is not the purpose to foster interdisciplinary territorial squabbles or facilitate medical market niches for any one medical subspecialty over another. Ultimately, provider competence and patient satisfaction (monitored by feedback database and medical outcomes database on each member) will be more influential with prospective buyers than certificates from obscure subspecialty entities. A prudent balance between qualifier threshold and the fostering of competitive markets are possible with the system 16 in accordance with the present invention.

The system 16 provides free system access to a plurality of prospective buyers for the purpose of viewing offered medical services. In order for a prospective buyer to purchase a listed service at a listed purchase price, or at any price, the prospective buyer of medical services must first enroll using an on-line registration system 84. Once enrolled (registered), a buyer is issued a buyer identifier and, using the identifier, may place an offer to purchase the listed medical service. The system receives the offer to buy, accompanied by a specified purchase price, from the buyer, and if the specified purchase price in the offer to buy the specified medical service is greater than or equal to the last bid price, the offer is accepted and stored in a transaction status database 76. The transaction status database 76 includes a processor that provides an output to the seller identifying the buyer and enabling direct communication therebetween. The parties to the closed transaction are then billed for system use via the transaction analysis and billing processing unit 77.

The method for buying and selling a medical service, described above, is efficient and has advantages realized by both the buyer and the seller. The seller can reduce advertising costs and use facility resources more efficiently. The buyer secures needed or desired medical services by accepting restrictions regarding when and where the service is provided as set forth in the specifications accompanying an offered medical service. The method may not in all instances, however, fully bring market forces to bear on the pricing of medical services. In the above example, the price is set by the medical service provider either at a "fixed" price or at the highest price proffered in a Dutch auction, and is either accepted or rejected by the buyer. The power of the present invention is better realized by opening the price of medical services to competitive bidding, most preferably in the form of an auction.

The above-described method for selling and acquiring medical services at a fixed price can be modified to meet objectives of the present invention by posting offers to sell medical services on a global database at an open, unspecified price that exceeds a fixed minimum reserve price. In accordance with the preferred method of the present invention, the enrollment and authentication of buyers and sellers is implemented as described above. The medical service provider (seller) submits an offer to sell specified medical services at a price to exceed a minimum reserve price. After the system 16 receives the offer and authenticates the medical service provider's qualifications to provide the medical service in the manner described above, the offer to sell is posted on a globally accessible offered service database 73.

A plurality of registered buyers 74, viewing the offer to sell, may submit an offer to buy the offered medical service. The purchase offer and the time that the offer is received by the system are stored. The proffered purchase price, specified in the offer to purchase, is compared with the reserve price specified by the seller. If the proffered purchase price is equal to or greater than the reserve price, the purchase offer is entered into the bidding database and the time that the offer was proffered is recorded. A second prospective buyer may view the first buyer's proffered offer and submit a second offer to purchase the medical service at a price that exceeds the price offered by the first prospective buyer. If the purchase offer proffered by the second buyer is greater than the price proffered by the first buyer, the offer proffered by the second buyer is entered and the first buyer notified that a higher bid was received. The first buyer, or any other buyer viewing the second buyer's offer, can proffer a third offer that exceeds the then-current highest offer. The process continues until the time allocated for closing the transaction, specified by the seller, has been reached, and further bidding is closed. As in the seller-fixed-price example of the method described earlier, the parties to the transaction are noticed that the transaction is complete and then they are billed at 77.

The provider feedback database 79 of the system 16, illustrated in FIG. 7, provides means for the buyer to comment on the transaction after the medical services are rendered, the comments providing feedback regarding provider performance which is stored in the database 79 for future reference. Transaction feedback may be stored separately from a medical outcomes database 79a which may take longer to acquire and derive meaningful data.

The method of the present invention also contemplates purchasing of medical services at a price determined by buyers. In this example of the method, a registered buyer 74 logs onto the system 16, selects a medical service that the buyer wishes to acquire and proffers a purchase price for the medical service. If the buyer is registered, the purchase offer is posted on a "services wanted" bidding database 75, which is accessible to a plurality of registered providers of medical services. If a provider viewing the offer to buy wishes to provide the medical service at the proffered seller-set price, the medical service provider submits an offer to sell the specified services to the system. After the medical service provider's qualifications for providing the medical service are authenticated by the system, the offer to sell is posted for viewing by the buyer. The buyer may either accept the offer to sell, and all conditions specified in the offer to sell, such as the location and date that the services will be rendered, or defer acceptance of a particular offer until a specified time. Further offers to sell medical services to the buyer may be submitted by qualified sellers until the time window specified by the buyer for receiving offers closes. The buyer may accept or reject any medical service provider's offer to sell without cause.

Any buyer, once registered, whether a patient, an agent of the patient or an insurer, may use the system and method of the present invention to bid for an offered medical service.

Figure 9:
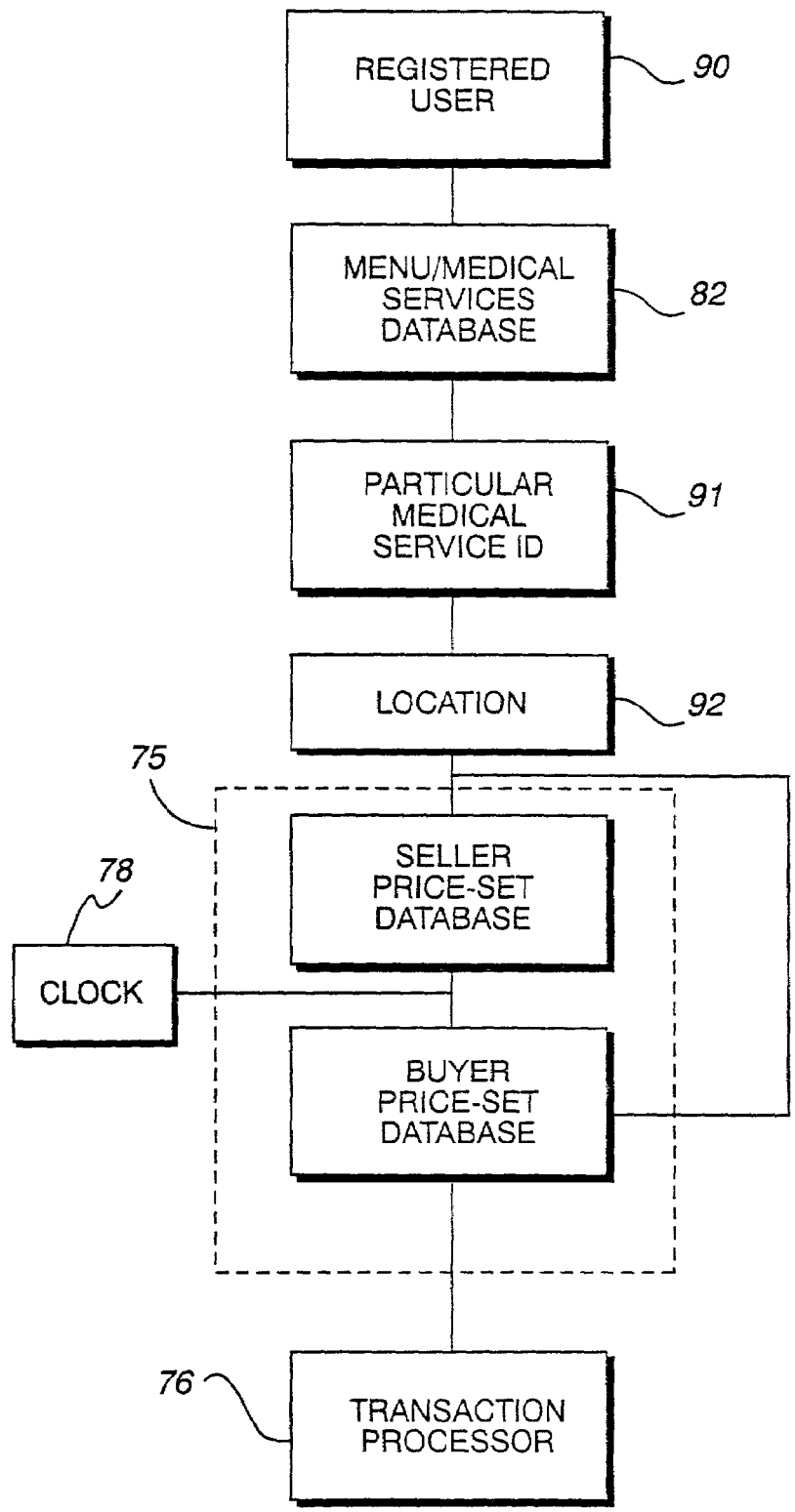
FIG. 9 is a block diagram of a presently preferred example embodiment of the present invention illustrating the interactive functional relationship between various components of the medical transaction system of the present invention.

The registered buyer may also use the system 16 to post an offer to purchase a specified medical service and solicit bids for the specified medical service from medical service providers. With reference now to FIG. 9, to use the system 16, the registered user 90 is linked to a menu 82 of medical services (shown in more detail at 83 in FIG. 8). The registered user 90 selects a particular medical service 91 from the menu 82 and is prompted to identify a location at 92, by city and state, where the particular medical service is to be rendered. The registered user is then provided with a choice of ways for offering to buy or sell the particular medical service 91. For example, a buyer may scan the offers to sell the particular medical service in the geographical area of interest that are posted on the bidding database. The buyer can either purchase the medical service at the price specified by the medical service provider or proffer a purchase price that is less than the specified selling price. The buyer's bid is compared with the highest previous bid received from other buyers which is stored in the bidding database, and either replaces the highest bid in the bidding database or is rejected. The bidder may be noticed of the previous highest bid prior to entering a bid thereby providing the opportunity to increase the bid.

If the medical service provider has specified a minimum reserve selling price which is greater than the proffered offering price, the proffered offer to purchase can, at the buyer's option, be posted in a buyer-priced database, and the offer to purchase made available for viewing by a plurality of registered medical service providers. A medical service provider viewing the offer to purchase may proffer an offer to sell the posted particular medical service, which offer is stored in the buyer-priced database. The prospective buyer is noticed of the proffer and may either accept or reject the proffer, along with the specifications connected to the proffer.

The formation of a legally binding contract between parties requires (a) mutual consent to the same terms and conditions; and (b) consideration. If the buy-sell transaction is conducted, in part, by electronic telecommunication, a practical system must additionally comply with the legal requirements for perfecting an agreement under electronic contracting law; an area of law that is evolving. Any agreement between a medical service provider and a patient and/or a patient's insurance company must provide for termination of the agreement in the event that either the medical risk for the patient has changed after the agreement was entered into and before services are to be rendered, or the medical service provider is unable to render the medical service at the time the service is to be performed for a cause reasonably beyond the control of the provider. These considerations, as well as means for dealing with them, are contemplated in the present invention.

The system presented herein provides flexibility for both the medical service provider and the buyer (or payor). For example, a provider may offer a package that includes surgery, a hospital bed (for x days), hospital services, anesthesia and operating room. Alternatively, the provider may offer the package and include the hospital bed for only one day after which the cost of the bed is extra. The buyer can search for a provider that is offering a hospital bed and services at a better price, and arrange to be transferred to the other hospital bed after the first day included within the contracted package has passed.

A low hospital bed occupation census is economically wasteful because the hospital must maintain full time staffing in a "ready mode", prepared to take care of various medical and surgical events during all shifts. The cost of maintaining such highly skilled labor and services is high, both in terms of monthly payroll and the cost of compliance with imposed regulatory procedures that a hospital must deal with. As an example, consider a well-staffed hospital experiencing a low patient census situation during the month of February. Such a low census could be a seasonally cyclical effect, or due to a slump in the local economy. A major managed care provider may have taken all its subscribers to a competing cross-town hospital that offered them a better per diem contract. Whatever the reason for the low patient census, the hospital must respond effectively or close its doors.

The hospital may respond to the low census event by posting an offer to sell ten medical patients per diem, each patient per diem including the cost of a hospital bed with included medical and nursing services, on "e-MedBid.com" at a reserve price of $800.00 per day. The usual per diem charge (i.e. base price) is $1800 per day. The offering hospital may expect to receive a per diem fee of $1560 from Medicare. The hospital may receive $1260 per diem from some managed care plan which would be marginal for meeting its operating costs. If a patient is admitted and needs costly care, the hospital loses money at that rate. Nevertheless, the hospital benefits the community by taking care of needy and uninsured patients and participates with dominant community insurance plans, even if they reimburse marginally.

An insurance carrier with a large population of subscribers may view the offer to sell and choose to bid for the offered $800 per diem beds with an intent to place its community subscribers in the offering hospital when such hospital services are needed. The insurance carrier may purchase all 10 beds by on-line bidding, benefiting from the sharply discounted per diem price. If the insurance carrier(s) utilize those beds, they will realize a profit. Hopefully, this will benefit the consumer through lower insurance premiums. The offered beds can also be bid for by uninsured patients (estimated 44 million) that seek an elective procedure and wish to reduce their out-of-pocket costs.

The same day/beds may be purchased or bid for by a cardiac surgeon who purchases cardiac/surgical per diems. Operating room hours and ICU beds may also be acquired in similar fashion. The surgeon, having purchased the beds, may then post an offer to provide (i.e. sell) a very competitive combined package of coronary bypass graft with the associated hospital beds for a 4 day stay. He may offer such a package at preferred price of $18,000, which would cover not only his services, but also the anticipated hospital services (that he acquired at a significant discount to make the total package more attractive). The forgoing exemplary transaction works for the hospital, the physician, and the cardiopulmonary staff. The consumer/patient who is undergoing elective coronary bypass graft, benefits from significant discounts by using an otherwise underutilized hospital and staff.

At the same time, the consumer/patient has an enhanced ability to evaluate the quality of the physician and the hospital through the associated qualifier database and patient feedback links. The qualifier engine and associated databases make the qualifications of both the physician providing the service and the treatment institution/facilities available to the consumer/patient. The foregoing example, illustrating the use of the present invention for buying and selling medical services, facilitates the delivery of quality health service at competitive prices. This is just one of many exemplary scenarios where the present invention can make consumer/patient benefits, the healthcare provider benefits, and the quality of services more transparent than ever before.

The bidders for the specified hospital beds may include patients who have a large co-pay or deductible and are under pressure to use cost effective services as well as patients that choose novel healthcare insurance policies that will evolve when consumer driven price/quality medical services, in accordance with the present invention, become available. Such novel insurance policies may include policies having limited lifetime benefits. A low cost insurance policy may be developed that offers a $100,000 lifetime benefit (similar to term life insurance) wherein the monthly premium increases in proportion to the diminishing residual lifetime benefit. The patient may purchase additional coverage in units of $100,000. Premium costs for such novel policies will be a function of age, risk factors, medical evaluation and residual coverage available under other policies. Such insurance policies will shift cost controls to patients (or their agents) and hereby facilitate the imposition of cost with quality controls on the healthcare providers.

The system and method described herein empowers the patient to impose cost constraints and quality assurance on each healthcare transaction. Thus, the patient is better positioned to press for improved quality and reduced price from the health care industry. Current managed care programs employ uninvolved managers to impose cost controls with the guise of quality on the healthcare provider and disempower the patient in the process. The system and method disclosed herein does what current systems fail to do: empower the patient to make cost and quality decisions about their own healthcare. Thirty years ago, healthcare providers strove for quality and gave minimal attention to cost controls. Today, healthcare providers strive for cost controls and give token attention to quality. Future healthcare delivery systems will need to embrace both quality and cost controls and empower the patient to choose the right balance between these two, historically polar, interactive forces.

As a further example of the flexibility the system offers, a patient requiring a medical service or procedure may select a hospital of choice and bid for a hospital bed therein. If the bid is accepted by the hospital, the patient may then solicit bids from physicians qualified to perform the procedure at the hospital. In this manner, a patient or payor may be able to perfect the provision of the medical service by modularizing the components of the service and acquiring each component separately by means of bidding.

Current insurance reimbursement policies and practice frequently cause delay in payment for the provider of the medical services. The cost of the "float" is currently carried by the medical service provider and inflates the cost of providing medical services. Similarly, the provider must bear a portion of the cost of negotiating the presently complex and cumbersome contractual relationship between providers and insurers. In accordance with the present invention, the parties to the bidding transaction may specify payment policy. For example, the provider may require a 10% deposit at the time the bidding closes with an additional 90% due prior to the scheduled date of service. In this way, costly last minute cancellations can be minimized. In this regard, it may also be desirable to establish the buyer's ability to pay the bid price for a medical service by searching a variety of databases containing member credit information prior to accepting the bid. Such search engines are well known in the prior art and may be linked to the system 16 electronically.

Figure 10:
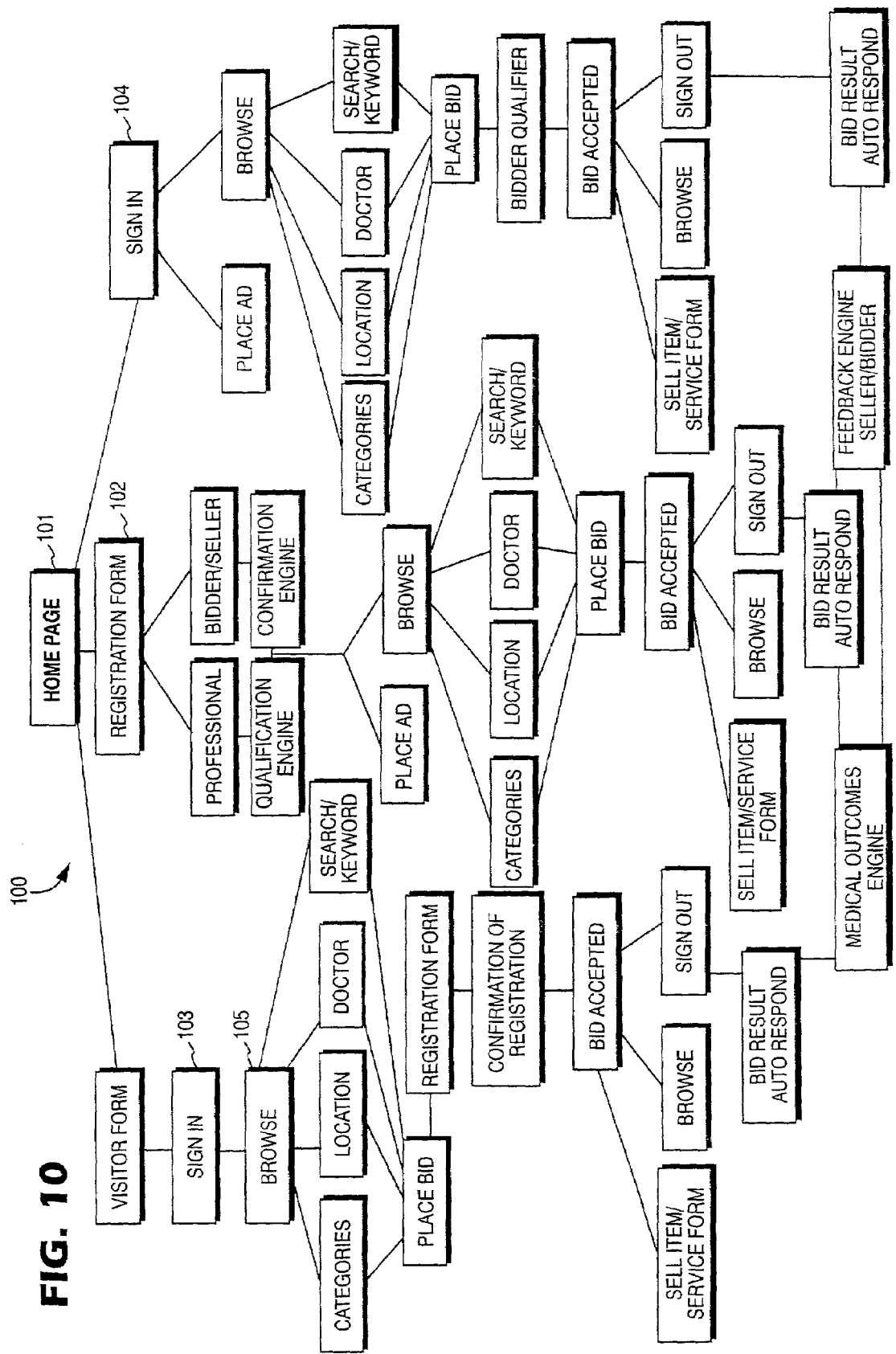
FIG. 10 is a block diagram illustrating example linking web pages accessible online via a web-site main page of the medical transaction system of the present invention.

FIG. 10 shows an hierarchical diagram of linked Internet "web" pages, illustrated as labeled blocks 100, for an example medical transaction system "web-site" provided by medical transaction system 16. Any person having a computer with an Internet connection and a conventional "browser" program can obtain access to the medical transaction system web-site as provided by the present invention. In this example, conventional HTML document "web" pages 100 are distributed via the Internet by transaction system 16. Hyper-text links (not shown) on the web pages allow an online "visitor" to view further web pages provided by medical transaction system 16 (as indicated by the connecting lines between labeled blocks 100). The various web-pages may be accessed, for example, by prospective bidders and service providers via the hyper-text links for obtaining specific information or performing a particular function. For example, an online "visitor" to the transaction system web site may begin an online session by receiving a "home page" 101 from which the visitor can access and view other "linked" pages for participating online in selected transactions and related activities such as: registering via an online registration form (102), identification as a registered user via "sign in" pages (103, 104), browsing for specific information (105), etc.

FIG. 11 shows another block diagram illustrating example functions 200 available to a visitor 201 upon accessing the exemplary medical transaction web-site of the present invention for performing various online functions.

Referring now to FIG. 11, a visitor to the sites, for example, a prospective bidder, service buyer, (e.g. insurance company) or a provider of medical services encounter registration forms upon entering the web site. The registration forms provided are different for a provider of services (who will also need to list their qualifications to provide such services) than for a buyer of services (who will need to establish credit worthiness and a certain threshold criteria and identification to make them an accreditable purchaser of services). This is done through the use of outside links with VISA, Mastercard and banking links to confirm the credibility of buyers in a similar fashion as a credit check engine are done at this time. A prospective purchaser of services may then enter a "posting" database 242 where procedures for bidding are made available to bidders and providers can post their services and their specific requirements/conditions.

At the posting database there are web page links 203 to individual provider web sites to further improve the depth of knowledge and qualifications of such provider. There is also provision for making an e-mail connection 204 with the proffered service providers if there are specific issues that need to be resolved, answered or negotiated between the bidder and the provider. Search engine 205 can search by categories, time, locations, and available services, as well as parameters that are linked to quality assurance. A quality assurance database 200 is linked to a provider member's database 207. Using this database, web pages are also provided for viewing comments and feedback associated with individual transaction and outcomes, as well as links to a software qualifier engine (authenticating engine) that evaluates each registered provider member through outside links to AMA, State Licensing, Federal Licensing, Hospital Privileges and certifying bodies.

Such multi-level confirmation to outside available database is done internally by transaction system 16 in the background through the qualifier engine. For example, system 16 performs a search in an outside Public domain database or subscribed databases using a registrant's name and license number. Confirmations are then displayed for the bidder/user of such services.

Upon registering a provider of proffered services lists his/her qualification, board certification and his/her hospital privileges. In the background, the qualifier engine 208 will reach out to existing databases in the network to determine if stated/listed qualifications of a particular service provider are confirmed and cross referenced on existing outside databases.

Subsequent bids on a given procedure are stored. There are various types of bidding process that may go on. They could be negotiated bids with counter offers. There could be a reserved bid where a provider lists his services with a hidden reserve price below which, until that price is reached, he is not obliged to consume the transaction and there is a Dutch bid in which a number of procedures or hospital beds can be listed at a given price and bidders bid at that price. If all the orders are filled they can voluntarily raise their price to secure a primary position in obtaining such limited services at the specified Dutch bid. In addition, there is a prior transaction database where assessment of similar procedures by similar providers can be traced historically. There is also a database for outcomes of such transactions in the feedback form.

Figure 13:
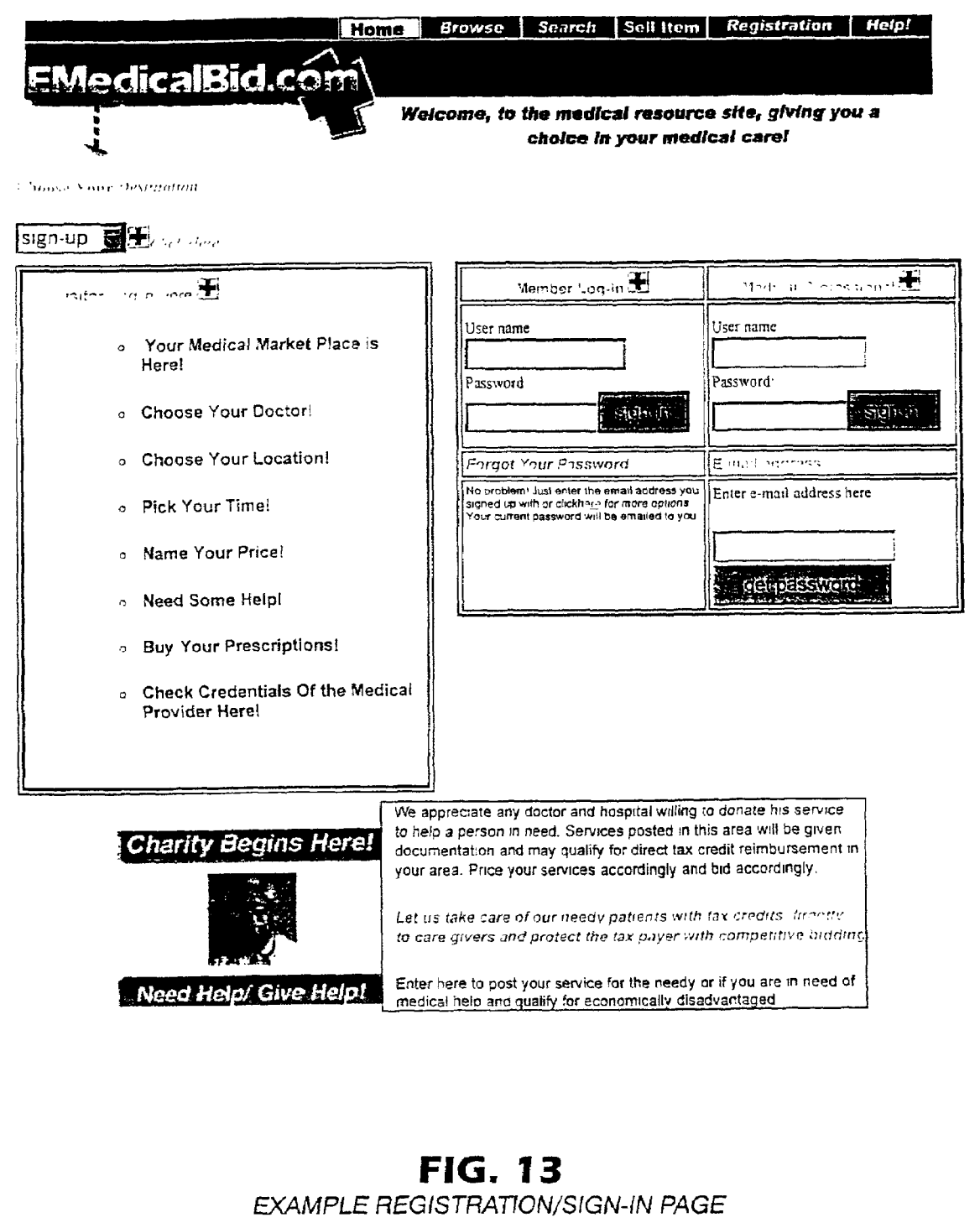

FIGS. 12 through 16 show example bitmapped image screenshots of various web pages provided by the medical transaction system of the present invention. FIG. 12 shows a bitmapped image screenshot of an example proffered services menu page ("Browse" page). In this example embodiment, the menu page includes lists of proffered medical services and products for selection by a prospective bidder. The menu page in this embodiment may also include a display section listing experimental treatments/studies where protocols, subject selection criterion, investigator qualifications and regulatory approvals are listed when available. In addition, the menu page in this embodiment may include user selection boxes for selecting a preferred location (e.g., by state) and a preferred time (e.g., by month) for the service to be performed. The menu page for the example embodiment may further include a display section listing "hot items" representing selected proffered services and/or medical products that are currently being offered at a low price representing a "good deal." The menu page for the example embodiment may also further include a display section for listing "wanted" items and/or services (i.e., desired items and/or services) along with a proffered price posted, for example, by a recent visitor to the web site. FIG. 13 shows a bitmapped image screenshot of an example visitor "Log-in" web page provided online for registered users of the medical transaction system of the present invention. FIG. 14 shows a bitmapped image screenshot of an example visitor "Registration" web page provided online. FIGS. 15A through 15D show bitmapped image screenshots of an example "Place-ad" page provided to a registered service provider and FIG. 16 shows a bitmapped image screenshot of an example "Search-item" page provided to a prospective patient/bidder.

The online transaction system of the present invention also provides an arrangement for handling and providing bid price modifications and variable pricing schemes to accommodate, for example, unanticipated changes in rendered medical procedures and medical procedures of various levels of complexity. For example, a gall bladder removal operation performed on a healthy person vs. a patient with a potentially affecting concurrent condition or illness (such as diabetes, hypertension or obesity) may require a different degree or level of care or even a different type of medical service or treatment than originally bid upon. For example, one type of service/treatment may be provided on an out-patient basis and another may require use of an acute care facility. Consequently, there is a need to disclose to a provider of proffered medical services at least some personal medical information concerning a prospective patient so that an equitable price or an adjustment to an offered price for proffered services can be made in the case where it is determined that unanticipated different or additional medical services must be rendered.

The need for a disclosure of personal medical information by a prospective patient or bidder can potentially pose a problem in an "anonymous" online bidding context since the personal privacy interests of prospective patients/bidders must somehow be protected. Although such information may significantly affect the ultimate cost of a proffered service, a prospective patient/bidder should not be required to disclose online detailed personal medical information before an actual patient/physician relationship is established. As an effective solution to this problem, the online transaction system of the present invention uses an online medical "complexity rating" that allows a bidder to communicate to a proffered service provider a scale value that is at least somewhat indicative of the degree to which undisclosed pre-existing/concurrent personal medical conditions may affect the proffered service. In an example embodiment, a prospective patient may select a complexity rating which best describes his/her concurrent medical condition or medical history from an online list provided by the transaction system. Once a patient/physician relationship is actually established, the selected complexity rating is later used by the transaction system in computing an adjustment to the bid price. The amount of the adjustment is subject to a complexity rating of the patient by the service provider after evaluating the patient.

Figure 17A:

For example, using a limited scale of values from zero to two, a medical complexity rating scale value of "0" might be used to define the medical situation of a standard healthy patient with no known concurrent medical conditions or problems (indicating no potentially complicating factors to treatment); a scale value of "1" might be used to define the medical situation of a patient with at least one concurrent medical condition or other associated medical problems (indicating some degree of medical complexity and potentially complicating factors to treatment); and, a scale value of "2" might be used to define the medical situation of a patient with multiple concurrent medical conditions, problems or history of prior failed treatments (indicating a medically complex situation with multiple factors contributing to the performance of the proffered service). A prospective patient/bidder, after reviewing the online complexity rating definitions, then selects and submits a complexity rating selection value—preferably along with his/her bid during the online bidding process. FIGS. 17A and 17B show a bit-mapped screen display of an example "bidding form" web page provided to an online bidder. In this example, complexity rating input box (300) is provided for selecting and submitting a complexity rating scale value.

At the time of registering with transaction system 16 and placing an online solicitation for offers to bid on a proffered service, a service provider may submit information relating to an amount or percentage of bid price adjustment to be made as a function of the increase (or decrease) in complexity of rendering a proffered service, based on the same medical concurrent complexity rating scale. FIG. 15D shows a bit-mapped screen display of a portion of an example place-ad/registration form web page provided to an online service provider. In this example, a portion of the provided web page place-ad/registration form includes a "Medical Concurrent Complexity Rating" scale definition (400) that is displayed, along with web page input boxes (401, 402, 403) below it, for selecting and submitting bid price adjustments to be made based on the complexity rating scale.

For example, if a provider lists a gallbladder operation where he can have an incremental increase depending on his fee and listed in the bid depending on the associated complexity. He can have a current status that is about 20% to 30% increase for level 1 complexity and possible a 40% increase for level 2 complexity. Level 1 complexity would be an associated medical condition that could impact the complexity of the given procedure. Such conditions could be diabetes, hypertension, bleeding disorders, cardiac disease or basically anyone who is taking other medical for other chronic medical conditions. This would be voluntarily listed as a category 1 of complexity. There is another level of complexity that would constitute a category 2 that not only involves specific conditions that would complicate a given treatment, but also a history of previous treatments, failed or successful for a given conditions.

An another example of such procedural "complexity" would be if a patient has undergone four rhinoplasties in the past and is shopping for the fifth. Obviously, this involves previous failed treatment. The area is full of scar tissue and a revision scar rhinoplasty is certainly not a virgin rhinoplasty. At the same token, the patient will submit voluntarily, his own assessment of complexity. In the feedback that the provider of services learns about the patient, he/she will list the complexity divergence score that after medical evaluation to describe whether the patient correctly described their level of complexity. This would constitute the market force to maintain honest communication yet, at the same time, disclose no specifics about a particular condition and, in the absence of specific information, privacy issues are not encountered. In this fashion, the patient voluntarily assesses his or her own level of complexity and communicates that to the provider. The provider has an automatic pricing adjustment, if he chooses, or he may choose to have it at the same price but at least the complexity issues are not negatively impacting the conditional bid transaction.

The condition aspect remains in force because the provider of services, or physician, has the ultimate liability to assess whether the given procedure is medically indicated even though the patient may have bid for it. he has to have the option to decline if he deems it an unnecessary risk to the patient's life or not medically indicated for the condition the patient is seeking. By the same token, the patient is protected that, in the event an alternative procedure is required, the patient will have an opportunity to receive that alternate procedure at the same price he bid for with the lesser procedure, with a relative value scale factor adjustment for the more complex procedure. This protects the pricing the patient has pursued and prevents the clinicians from unnecessarily "upcoding" the complexity or negotiating a new deal once the patient is in their office. CPT coding for procedures I already establish where it's a database of a description and codes. A standard word search can be utilized to locate the appropriate codes to describe a given procedure.

Once a patient/physician relationship is established between a bidder and a service provider (assuming, for example, the provider/physician has physically examined and evaluated the patient), the service provider/physician similarly submits a complexity rating scale value online to the transaction system based on an assessment of the patient (patient evaluation feedback). The transaction system then uses the respective complexity rating scale values submitted by both the patient/bidder and the service provider/physician to compute a "complexity divergence" score. This value may be based, for example, on the difference between the complexity rating scale value submitted by the patient and the complexity rating scale value submitted by the provider. The transaction system may also compute a cumulative divergence score based, for example, on a running average of complexity divergence scores associated with a particular patient over a series of separate medical transactions.

Transaction system 16 also provides various web page based online "feedback" mechanisms for both the patient and the provider. For example, FIG. 18 shows a bit-mapped screen display of an example Bidder Feedback form web page provided online to a registered bidder. The example form includes drop-down input selection boxes for allowing a registered bidder to select various predefined descriptions of the bidder's perceived quality of service provided by a particular service provider. For example, one or more an input/selection boxes are provided for identifying: the particular service provider used, the service category involved, the ease/difficulty of conducting the particular transaction (transaction ease), the outcome of the treatment (treatment outcome) and providing suggestions/comments about or for the service provider.

Figure 19:
FIG. 19 is a bitmapped image screenshot of an example Provider's Feedback Form web page provided to an online registered service provider.

Provisions are also made for allowing a service provider to provide comments/feedback regarding a particular patient. For example, FIG. 19 shows a bit-mapped screen display of an example Provider's Feedback Form web page provided online to a registered service provider. Using a "patient's compliance" input box displayed on a web page provided by the transaction system to a registered service provider, the provider may submit feedback to the transaction system such as, for example, various comments/information regarding a particular patient's ability to follow instructions and take appropriate medication.

The following example illustrates the use of the complexity and divergence score: A patient shopping for a rhinoplasty bids for a rhinoplasty from a skilled practitioner and represents himself as a complexity level 0. At the time of consultation, it turns out that the patient has had three fractures and four previous operations. He now has a fair amount of scarring and complexity. The chances of getting good results are borderline. The practitioner now has the medical obligation to inform the patient of the complexity of his condition. In the example, there is a divergence of 2. At this point, the practitioner has the choice of not performing the procedure (if he feels the risks are too high) or if an understanding with the bidder can be reached he may perform the procedure (a higher level of complexity). This new negotiated price, for example, would be bound by published CPT codes and a "relative value multiplier". For example, if a simple procedure is to be performed at $3000, and two levels of complexity imply a 40% increase, the new price will reflect compliance with the relative value scale and then increase it by the percentage of points against the lesser procedure. The incorporation of these concepts is illustrated in FIGS. 18 and 19 by the bidder and provider feedback forms.

Procedural CPT codes are a set of complex codes developed to help insurance companies code medical procedures in their attempt to standardize reimbursements. Transaction system 16 may incorporate a CPT coding/search engine that provides the CPT code number associated with a particular medical procedure. The proffered service provider may optionally list relevant CPT codes that describe the procedure he/she is putting up for bid. In a contract, for example, the provider of services agrees to follow conventional published "relative value" guidelines in the event that the bidder medically ultimately needs a related CPT code medical service instead of the proffered service upon which the bid was based. (There are several published "relative value scales", for example, McGraw Hill, which tries to standardize the relative multiplier factors of one CPT code against another.) For example, a hernia operation may be a multiplier of 1.2 relative to a tonsillectomy. This feature is useful for handling the situation where a bidder for medical services bids for a procedure of lower complexity and is a holder of a contingent bid, and at the time of the consultation and finalization it is perceived through the medical practitioner that a patient has asked for one operation but actually to treat his condition, needs another.

For example, in order to set guide lines for such further negotiation on pricing and to protect the bidder from having the health provider inequitably increase the price for a related procedure, the provider of services is bound by his/her contract to utilize the published relative value multipliers. If the bidder requires another medical service that is related but of different complexity, the bidder has the option to accept the negotiated price of a different CPT coded procedure, but is bound by the relative value multipliers against the same price that was bid on the lesser procedure.

This arrangement protects the bidder from the dilemma of contingent bids if he/she requires another medical service than what he/she bids for, and it protects him/her from upper pricing related service by the provider. By the same token, it allows the provider to judiciously use his medical knowledge and perform appropriate procedures on his patient under guidelines of current medical standards and not be subject to bids that the patients may have chosen. This arrangement offers both the flexibility of judicious medical choices, yet protects the consumer from an inequitable pricing fluctuation of the bid price.

The present invention can produce a lowering in the cost for provision of medical services in at least the following ways: First, bringing market forces to bear on the price of medical services will produce a downward pressure on the cost of such services. Second, medical resources at a given service facility can be allocated more efficiently, thereby reducing costly "down time". Third, the online medical transaction system of the present invention can reduce a service provider's non-productive costs associated with carrying a "float" and reduce or eliminate the cost of entering into complex agreements with insurers. The savings made possible by the present invention may enable a greater share of the limited healthcare market dollars to be spent on delivering needed health care rather than on contracts, appeals and marketing expenses.

The skilled artisan will appreciate that the apparatus and method of the present invention may easily be adapted for use in the fields of legal services (e.g. lawbid.com) and accounting services, where it may be desirable to permit market forces to impact cost of service. Introduction of market forces to legal and accounting services for the control of pricing will greatly enhance transaction efficiency and broaden the availability of such services to both the buyer and supplier.

While particular embodiments of the present invention have been illustrated and described, it will be obvious to those skilled in the art that various other changes and modifications can be made without departing from the spirit and scope of the invention. The appended claims are therefore intended to cover all such changes and modifications.

What is claimed is:

1. An online computerized method for arranging scheduled delivery of personal medical services from a provider having verified qualifications, said method comprising:
   registering a medical service provider and automatically authenticating qualifications of said medical service provider to perform a proffered medical service upon obtaining registration information from said provider;
   posting online at least one proffered personal medical service in association with a provider of such service after having verified the service provider's qualifications for providing such service; and
   receiving online bids for such service as proffered by prospective users of such service.

2. An online computerized method as in claim 1 wherein said posting includes proffered specifications received in association with provision of said proffered service.

3. An online computerized method as in claim 2 wherein said proffered specifications include price, time and location for provision the service.

4. An online computerized method as in claim 3 wherein said price is automatically computed based on at least one: (a) projected future utilization of the service provider's facility, (b) a predetermined minimum price, and (c) a predetermined base price.

5. An online computerized method as in claim 4 wherein said price is computed as a function of the base price plus a fraction of the difference between the minimum price and the base price, said fraction being related to projected future utilization of the service provider's facility.

6. An online computerized method as in claim 3 wherein said proffered specifications include conditions precedent to the provision of said service, said conditions precedent including the health and suitability of the prospective user for receiving the proffered service.

7. An online computerized method as in claim 3 further comprising:
   in response to tentative online agreement between a prospective service provider and a prospective user, providing contract details to the provider and/or user to permit direct follow-up communication therebetween to finalize the tentative online agreement.

8. An online computerized method as in claim 3 wherein said proffered specifications include terms of payment.

9. An online computerized method as in claim 8 wherein said terms of payment include a requirement for at least partial advance payment before the service is provided.

10. An online computerized method as in claim 1 further comprising:
    obtaining online information about the service provider as supplied by prior users of such service provider and making such information available online to prospective bidders for such service.

11. An online computerized method as in claim 1 wherein said posting includes a posting of feedback information about the service provider as supplied by prior users of such service provider.

12. An online computerized method as in claim 1 further comprising:
    obtaining online information about the prospective users health and/or financial condition and supplying such information to said service provider for use in determining an online response to the prospective user's bid for service provision.

13. An online computerized method as in claim 1 further comprising:
    providing CPT and/or ICD-9 coding support for use in selecting proffered medical services.

14. An online computerized method as in claim 1 wherein said posting includes a posting of CPT and/or ICD-9 codes associated with proffered medical services.

15. An online computerized method as in claim 1 further comprising:
    obtaining a performance price of donated and/or discounted services performed by a provider of a personal medical service for use in logging or tracking tax credit information.

16. An online computerized method as in claim 1 wherein said receiving online bids includes limiting received bids for a particular proffered service to a predetermined response time window.

17. An online computerized method as in claim 16 wherein said response time window is dependent upon a receiving time of a previous bid.

18. An online computerized method for arranging delivery of medical services to prospective patients having ascertained health and/or financial condition information associated therewith, said method comprising:

posting online at least one medical service provider along with an associated proffered medical service;

receiving online bids as proffered by prospective patients of a service provider for delivery of a specified medical service;

in response to receiving an online bid, automatically accessing a maintained database and/or one or more online commercial data resources to obtain information describing the health and/or financial condition of a bid-submitting prospective patient; and forwarding a received online bid to an associated medical service provider together with the information describing the health and/or financial condition of the prospective patient associated with said forwarded bid.

19. A computerized method for selling a qualified personal medical service selected from a menu of authenticated qualified personal medical services, the menu of authenticated qualified medical services being accessible to prospective buyers of personal medical services, comprising the steps performed by a computer of:

(a) receiving from one or more medical service providers an offer to sell a specified personal medical service included within the menu of medical services at a specified offering price;

(b) accessing one or more online commercial database sources containing medical certifications data and verifying the authenticity of qualifications of the medical service provider to provide the specified personal medical service; and (c) if qualified, posting the offer to sell the specified personal medical service and the specified offering price in a database of authenticated qualified medical services that is accessible to a plurality of prospective buyers.

20. A method for selling a qualified personal medical service as in claim 19 further comprising enrolling a plurality of sellers of medical services using an Internet accessible on-line registration system.

21. A method for selling a qualified personal medical service as in claim 19 further comprising enrolling a plurality of buyers of medical services using an Internet accessible on-line registration system.

22. A method as in claim 19 further comprising receiving an offer to buy the qualified medical service posted on the database from a first buyer, said offer to buy including a specified purchase price.

23. A method as in claim 22 further comprising:

comparing the specified purchase price in the offer to buy with the specified offering price of the specified medical service, and if the specified purchase price is greater than or equal to the specified offering price, storing the offer to buy received from the first buyer on a computer readable medium and communicating the offer to buy to the medical service provider.

24. A system enabling a qualified medical service provider that has been authenticated as qualified to offer a specified medical service for sale to a plurality of prospective buyers of the specified personal medical service, said system comprising:

(a) a computer having an on-line connection;

(b) a computer-readable storage device connected to said computer;

(c) a program for controlling said computer;

(d) a register associated with said computer for establishing a computer-readable medical service provider identification code associated to a medical service provider; and (e) a service provider qualifier database accessible by said computer, said qualifier database containing information for identifying one or more medical service providers having credentials previously verified as acceptable for rendering said specified medical service and/or information for automatically verifying credentials of said service providers via other on-line sources; wherein the program is operable for causing the computer to:

(i) receive an on-line offer to sell the specified medical service and receive said medical service provider identification code from the medical service provider for verifying the identity of said medical service provider;

(ii) verify that the medical service provider is qualified to provide the offered specified medical service by using information stored in said service provider qualifier database; and (iii) post an offer to sell the specified medical service proffered by a service provider verified in step (ii) on a database that is accessible for on-line viewing by a plurality of prospective buyers of the specified medical service.

25. An online computerized method for arranging delivery of personal medical services with provision of online patient-compliance feedback information from a medical service provider for future use in evaluating future bids for delivery of personal medical services, said method comprising:

registering at least one medical service provider;

posting online at least one proffered personal medical service in association with a registered provider of such service;

receiving online bids for such service as proffered by prospective patients of such service provider; and after such service is provided to a prospective patient, receiving online and collecting into a database feedback information from such service provider regarding compliance of said patient with recommended medical procedures and/or physician instructions as given by such provider during course of treatment.

26. An online computerized method as in claim 25 wherein said patient-compliance feedback information is made available online to other service providers.

27. An online computerized method for arranging delivery of personal medical services with provision of online transaction outcome feedback information from a medical service provider for future use in evaluating future bids for delivery of personal medical services, said method comprising:

registering at least one medical service provider;

posting online at least one proffered personal medical service in association with a registered provider of such service;

receiving online bids for such service as proffered by prospective patients of such service provider; and after such service is provided to a prospective patient, receiving online and collecting into a database feedback information from such service provider describing a resultant outcome of providing a proffered medical service to said patient, wherein said feedback information is made available online at least to other prospective patients.

28. An online computerized method as in claim 27 wherein said transaction outcome feedback information is made available online to said service provider.

29. An online computerized method for arranging delivery of personal medical services with provision of online transaction outcome feedback information from a treated patient for future use in evaluating possible future bids for delivery of personal medical services, said method comprising:
- registering at least one medical service provider;
- posting online at least one proffered personal medical service in association with a registered provider of such service;
- receiving online bids for such service as proffered by prospective patients of such service provider; and
- after such service is provided to a prospective patient receiving online and collecting into a database feedback information from said patient describing a resultant outcome of receiving a proffered medical service from such service provider, wherein said information is made available online at least to other prospective patients.

30. An online computerized method as in claim 29 wherein said outcome feedback information is made available online to other prospective patients by posting said information online in association with said provider of such service.

31. An online computerized method for arranging delivery of personal medical services at a price which can be adjusted in a pre-arranged manner if unexpected circumstances arise in the delivery of such services, said method comprising:
- registering at least one medical service provider;
- posting online at least one proffered personal medical service in association with a registered provider of such service;
- receiving online bids for such service as proffered by prospective patients of such service provider for stated prices; and
- after a provider accepts a bid price for such proffered service, if a different or altered service is required to be rendered in response to said bid, computing an adjusted bid price based on a relative value multiplier, wherein said relative value multiplier is based upon a conventional procedural CPT code Relative Value Scale.

32. An online computerized method as in claim 31 wherein said conventional procedural CPT code Relative Value Scale information is made available online to prospective patients.

33. An online computerized method as in claim 31 wherein said adjusted bid price scale information is made available online to a patient receiving such rendered service.

* * * * *